(12) United States Patent
Arita et al.

(10) Patent No.: US 11,760,711 B2
(45) Date of Patent: *Sep. 19, 2023

(54) EPOXY COMPOUND, COMPOSITION, CURED PRODUCT AND LAMINATE

(71) Applicant: DIC Corporation, Tokyo (JP)

(72) Inventors: Kazuo Arita, Sakura (JP); Masato Otsu, Sakura (JP); Etsuko Suzuki, Sakura (JP)

(73) Assignee: DIC Corporation, Tokyo (JP)

(*) Notice: Subject to any disclaimer, the term of this patent is extended or adjusted under 35 U.S.C. 154(b) by 492 days.

This patent is subject to a terminal disclaimer.

(21) Appl. No.: 16/772,858

(22) PCT Filed: Nov. 20, 2018

(86) PCT No.: PCT/JP2018/042784
§ 371 (c)(1),
(2) Date: Jun. 15, 2020

(87) PCT Pub. No.: WO2019/123941
PCT Pub. Date: Jun. 27, 2019

(65) Prior Publication Data
US 2020/0331832 A1    Oct. 22, 2020

(30) Foreign Application Priority Data
Dec. 18, 2017 (JP) .................. 2017-241759

(51) Int. Cl.
*B32B 15/092* (2006.01)
*B32B 27/38* (2006.01)
*C08G 59/24* (2006.01)
*C08G 59/32* (2006.01)
*C09J 163/00* (2006.01)
*C08L 63/00* (2006.01)
*C07C 43/23* (2006.01)
*C08K 3/013* (2018.01)
*B32B 7/12* (2006.01)
*B32B 15/20* (2006.01)
*C08G 59/46* (2006.01)
*H05K 1/03* (2006.01)

(52) U.S. Cl.
CPC .............. *C07C 43/23* (2013.01); *B32B 7/12* (2013.01); *B32B 15/092* (2013.01); *B32B 15/20* (2013.01); *B32B 27/38* (2013.01); *C08G 59/3218* (2013.01); *C08G 59/46* (2013.01); *C08K 3/013* (2018.01); *C09J 163/00* (2013.01); *H05K 1/0373* (2013.01); *B32B 2250/40* (2013.01); *B32B 2457/08* (2013.01); *C08G 2170/00* (2013.01)

(58) Field of Classification Search
CPC .... C08G 59/02; C08G 59/066; C08G 59/245; C08G 59/3218; C07C 43/02; C07C 43/20; C07C 43/202; C07C 43/205; C07C 43/2055; C07C 43/23; C08L 63/00; C09J 163/00; B32B 15/092; B32B 27/38
USPC .......... 523/427, 428; 428/413, 414, 416, 418
See application file for complete search history.

(56) References Cited

U.S. PATENT DOCUMENTS 4,868,230 A * 9/1989 Rao ....................... C08G 59/066
523/403
2021/0269583 A1 * 9/2021 Otsu ..................... B32B 19/041

FOREIGN PATENT DOCUMENTS

JP    H08-53533 A     2/1996
JP    2006-335796 A   12/2006

OTHER PUBLICATIONS

International Search Report dated Feb. 26, 2019, issued for PCT/JP2018/042784.

* cited by examiner

*Primary Examiner* — Michael J Feely
(74) *Attorney, Agent, or Firm* — Locke Lord LLP; James E. Armstrong, IV; Nicholas J. DiCeglie, Jr.

(57) ABSTRACT

The invention provides an epoxy compound A represented by the following formula (1):

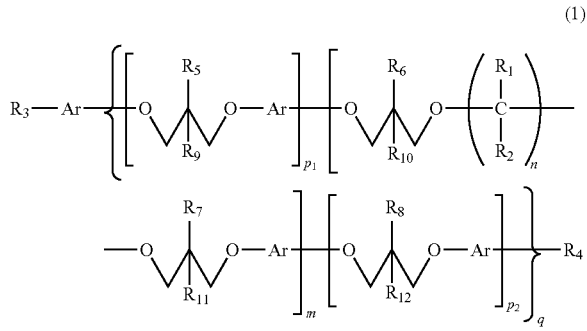

in the formula (1), Ar's each independently represent a structure having an unsubstituted or substituted aromatic ring; $R_1$ and $R_2$ each independently represent a hydrogen atom or an alkyl group having 1 or 2 carbon atoms; $R_3$ to $R_8$ represent a hydroxy group, a glycidyl ether group and/or a 2-methylglycidyl ether group, and at least one of $R_3$ to $R_8$ is a glycidyl ether group or a 2-methylglycidyl ether group; $R_9$ to $R_{12}$ represent a hydroxy group or a methyl group; n is an integer of 11 to 16; and m, $p_1$, $p_2$, and q are average values of repetition, m is 0.5 to 10, $p_1$ and $p_2$ are each independently 0 to 5, and q is 0.5 to 5 (provided that each repeating unit present in the repeating units may be the same or different).

24 Claims, No Drawings

EPOXY COMPOUND, COMPOSITION, CURED PRODUCT AND LAMINATE

TECHNICAL FIELD

The present invention relates to an epoxy compound having a specific structure, a composition containing the epoxy compound, and a cured product obtained by curing the composition. The present invention also relates to a laminate having the cured product layer.

BACKGROUND ART

In order to reduce $CO_2$ and improve fuel efficiency, the weight of automobiles and airplanes has been increasingly reduced. Accordingly, the number of spot welds has been reduced and the weight of automobiles and airplanes has been reduced by using a fiber-reinforced resin and a metal in combination, and there is a strong demand for higher performance of adhesives for structural materials used in these applications. In particular, in thermal bonding between aluminum and a fiber-reinforced resin, which have a large difference in thermal expansion, the occurrence of warpage and waviness due to interface stress caused by expansion and contraction is regarded as a problem, and an adhesive for relieving stress is required.

In addition, in advanced electronic materials used for semiconductor encapsulating materials, insulating layers for multilayer printed circuit boards, and the like, warpage due to a difference in thermal expansion between a silicon chip and a metal has become a serious problem due to the influence of the ultra-thin thickness, and a stress relaxation function has been required more than ever.

On the other hand, epoxy resins are widely used as adhesives because of their dimensional stability during curing, electrical insulation, and chemical resistance. However, since maintaining high adhesiveness results in solid and brittle, flexible epoxy compounds such as a polymerized epoxy compound obtained by reacting a liquid bisphenol A type epoxy resin with an aliphatic dicarboxylic acid such as dimer acid or sebacic acid as a molecular chain extender (for example, see PTL 1) and a polymerized epoxy compound derived from a hydroxy compound having an aliphatic hydrocarbon group (see PTL 2) have been disclosed. However, since the deformation mode of the flexible epoxy compound is plastic deformation, the epoxy compound cannot repeatedly follow the expansion difference from the substrate while maintaining the entire rigidity, and there is a problem in durability.

As described above, there is a demand for an epoxy compound that provides a flexible cured product having both a high elongation based on elastic deformation and high adhesiveness capable of withstanding a difference in thermal expansion from the substrate.

CITATION LIST

Patent Literature

PTL 1: JP-A-8-53533
PTL 2: JP-A-2006-335796

SUMMARY OF INVENTION

Technical Problem

An object of the present invention is to provide an epoxy compound capable of providing a flexible cured product having both a high elongation based on elastic deformation and a high adhesiveness capable of withstanding a difference in thermal expansion from the substrate.

The present invention also provides a composition containing the epoxy compound, a cured product obtained by curing the composition, and a laminate having the cured product layer and a substrate.

Solution to Problem

As a result of intensive studies, the present inventors have found that the above problems can be solved by providing an epoxy compound A represented by the following formula (1). That is, the present invention provides an epoxy compound A having a structure of the general formula (1).

[Chem. 1]

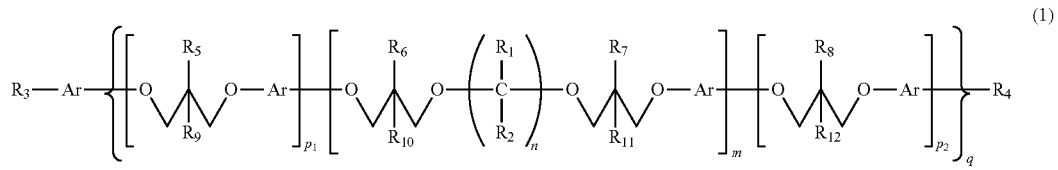

(1)

In the formula (1), Ar's each independently represent a structure having an aromatic ring; $R_1$ and $R_2$ each independently represent a hydrogen atom or an alkyl group having 1 or 2 carbon atoms; $R_3$ to $R_8$ represent a hydroxy group, a glycidyl ether group and/or a 2-methylglycidyl ether group, and at least one of $R_3$ to $R_8$ is a glycidyl ether group or a 2-methylglycidyl ether group; $R_9$ to $R_{12}$ represent a hydrogen atom or a methyl group; n is an integer of 11 to 16; and m, $p_1$, $p_2$, and q are average values of repetition, m is 0.5 to 10, $p_1$ and $p_2$ are each independently 0 to 5, and q is 0.5 to 5 (provided that each repeating unit present in the repeating units may be the same or different).

Further, the present invention also provides a composition containing the epoxy compound, a cured product obtained by curing the composition, and a laminate having the cured product layer and a substrate, and solves the above problem.

Advantageous Effects of Invention

The epoxy compound A of the present invention can provide a flexible cured product having both a high elongation based on elastic deformation and a high adhesiveness capable of withstanding a difference in thermal expansion from the substrate.

DESCRIPTION OF EMBODIMENTS

<Epoxy Compound A>

The epoxy compound A of the present invention is a compound represented by the following formula (1).

[Chem. 2]

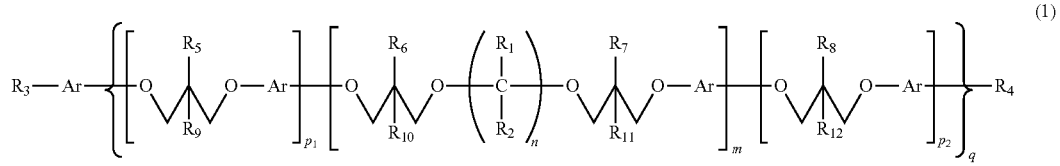

In the formula (1), Ar's each independently represent a structure having an aromatic ring; $R_1$ and $R_2$ each independently represent a hydrogen atom or an alkyl group having 1 or 2 carbon atoms; $R_3$ to $R_8$ represent a hydroxy group, a glycidyl ether group and/or a 2-methylglycidyl ether group, and at least one of $R_3$ to $R_8$ is a glycidyl ether group or a 2-methylglycidyl ether group; $R_9$ to $R_{12}$ represent a hydrogen atom hydroxy group or a methyl group; n is an integer of 11 to 16; m, $p_1$, $p_2$, and q are average values of repetition, m is 0.5 to 10, $p_1$ and $p_2$ are each independently 0 to 5, and q is 0.5 to 5 (provided that each repeating unit present in the repeating units may be the same or different).

Among these, the epoxy compound A having an epoxy equivalent of 150 to 900 g/eq is preferable because the cross-linking density of the obtained cured product is appropriate and both flexible toughness and heat resistance can be achieved.

In the general formula (1), Ar's each independently represent a structure having an unsubstituted or substituted aromatic ring. Examples of the aromatic ring include a benzene ring, a naphthalene ring, an anthracene ring, a phenanthrene ring, and a fluorene ring. Ar having an aromatic ring preferably represents any structure represented by the following formula (2).

[Chem. 3]

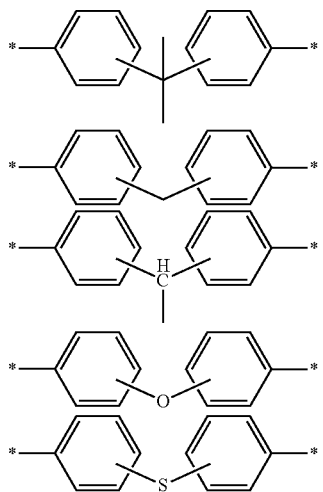

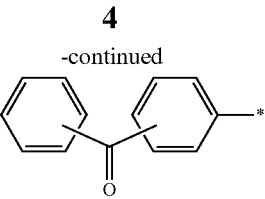

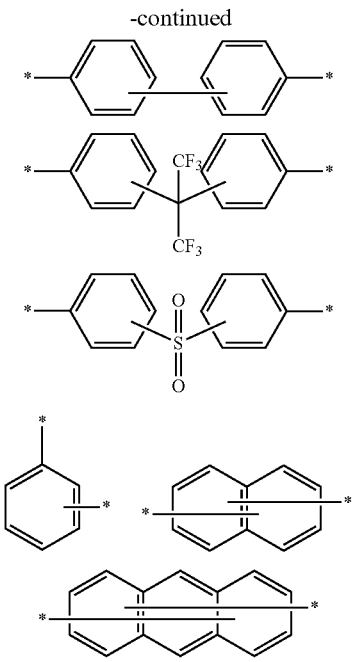

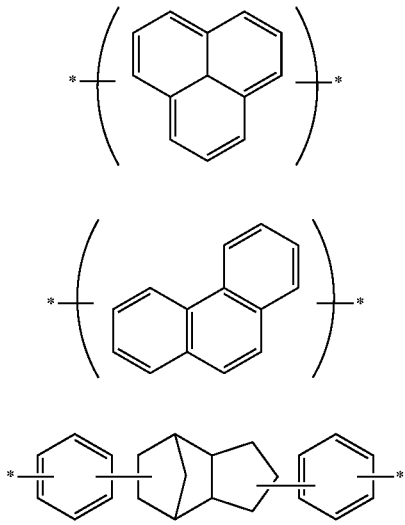

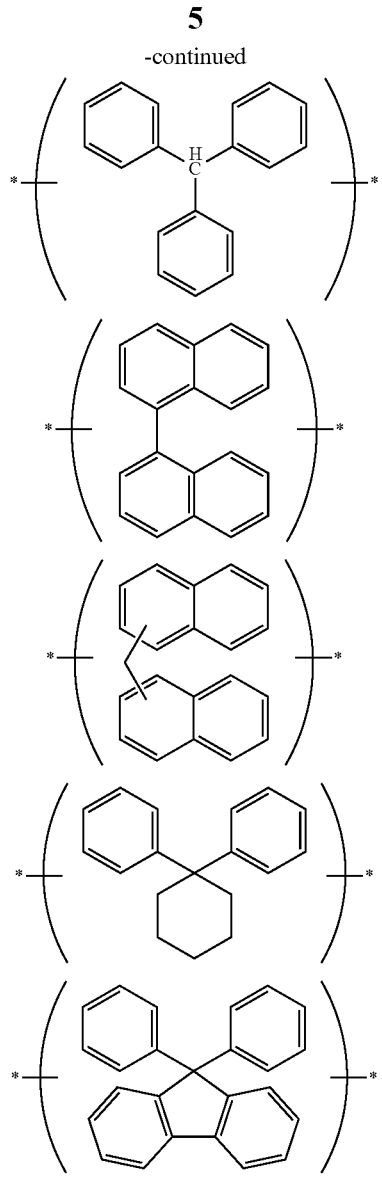

In the formula (2), the aromatic ring may be substituted or unsubstituted, and * represents a bonding point.

In the above formula (2), the structure of Ar is particularly preferably as follows from the viewpoint of excellent balance among flexibility, elastic modulus, and adhesiveness of the cured product.

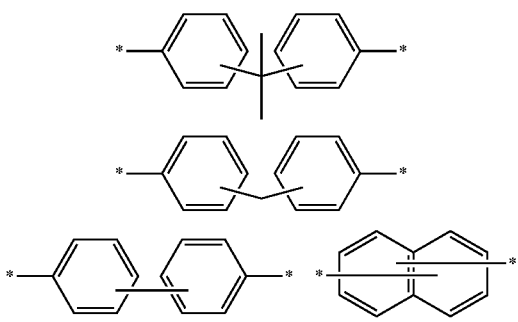

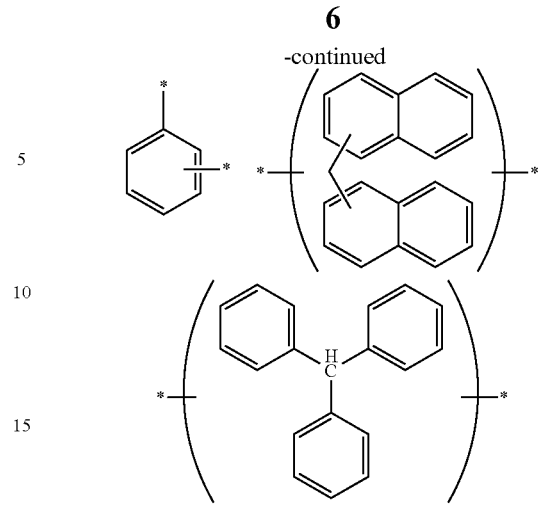

When Ar has a substituent, preferred examples of the substituent include an alkyl group, a halogen atom, a glycidyl ether group, and a 2-methylglycidyl ether group. An alkyl group, a glycidyl ether group, and a 2-methylglycidyl ether group are preferred, and a glycidyl ether group and/or a 2-methylglycidyl ether group are particularly preferred because the obtained cured product has excellent dimensional stability.

Particularly preferred examples of Ar having a substituent include the following structures.

[Chem. 4]

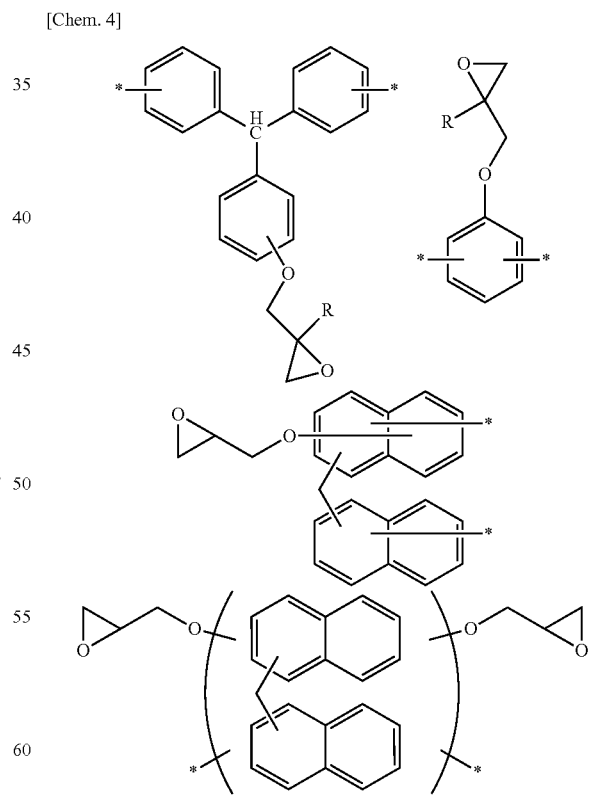

In the epoxy compound A represented by the formula (1), the repeating unit n is an integer of 11 to 16, preferably 12 to 15. When n is 11 or more, the adhesive force is improved, and the deformation mode of the cured product becomes elastic deformation. In addition, when n is 16 or less, a decrease in crosslinking density can be suppressed.

In the epoxy compound A represented by the formula (1), m, $p_1$, $p_2$, and q are average values of repetition, and m is 0.5 to 10, $p_1$ and $p_2$ are each independently 0 to 5, and q is 0.5 to 5.

The average value of repetition can be obtained by measuring with GPC. As for m, $p_1$, $p_2$, and q, m is preferably 0.6 to 5.0, $p_1$ and $p_2$ are preferably 0.5 to 3.0, and q is preferably 0.6 to 3.0 from the viewpoint of achieving both flexible toughness and durability.

In the epoxy compound A represented by the formula (1), $R_1$ and $R_2$ each independently represent a hydrogen atom or an alkyl group having 1 or 2 carbon atoms, $R_3$ to $R_8$ each represent a hydroxy group, a glycidyl ether group or a 2-methylglycidyl ether group, and at least one of $R_3$ to $R_8$ represents a glycidyl ether group or a 2-methylglycidyl ether group, and $R_9$ to $R_{12}$ each represent a hydroxy group or a methyl group.

Preferred structures of the epoxy compound A represented by the formula (1) include the following structures.

[Chem. 5]

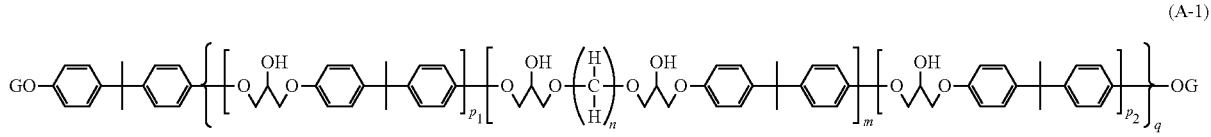

(A-1)

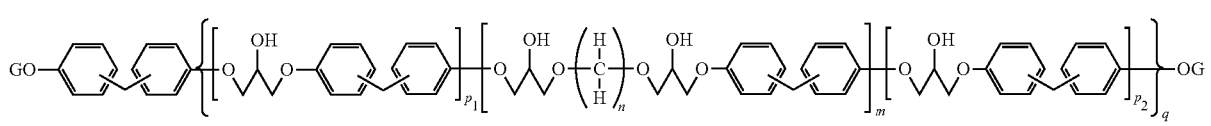

(A-2)

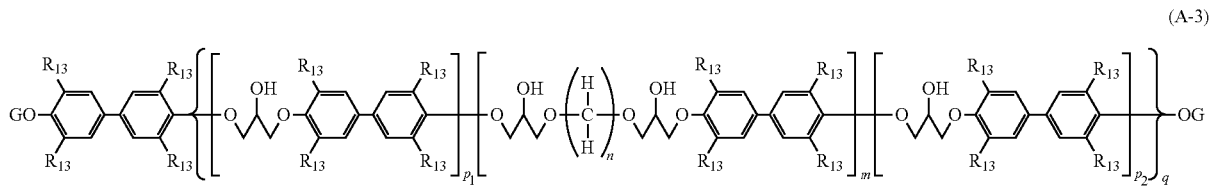

(A-3)

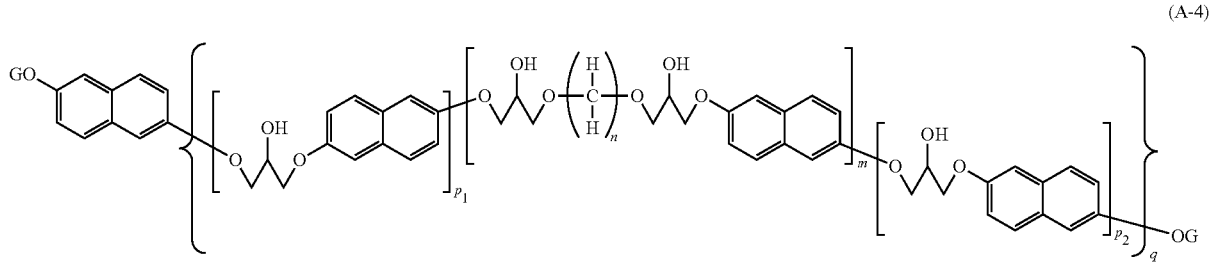

(A-4)

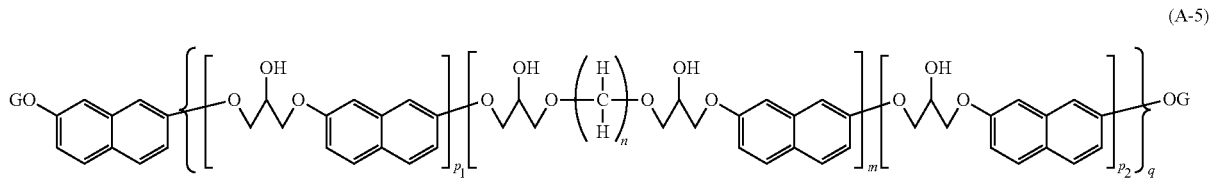

(A-5)

[Chem. 6]

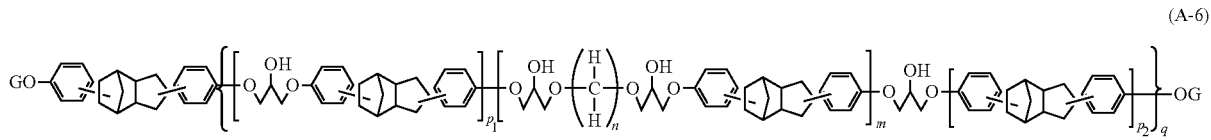

(A-6)

-continued
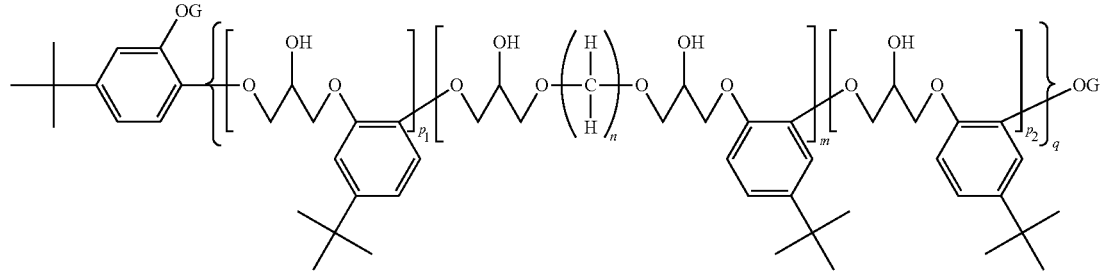
(A-7)
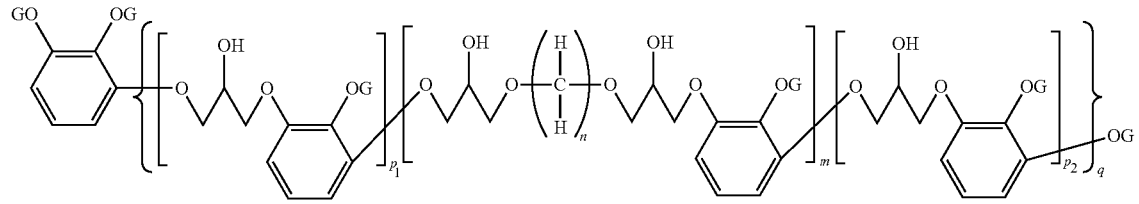
(A-8)
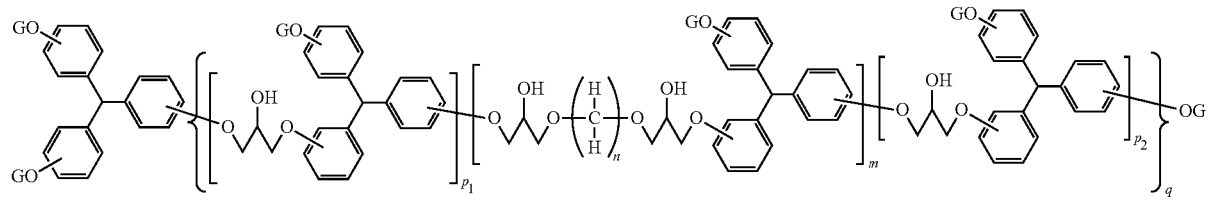
(A-9)
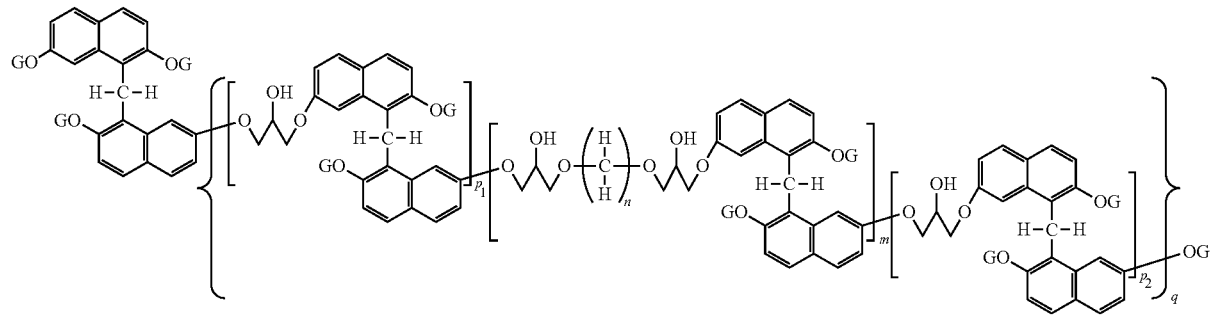
(A-10)
[Chem. 7]
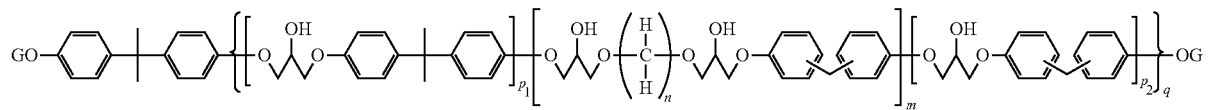
(A-11)
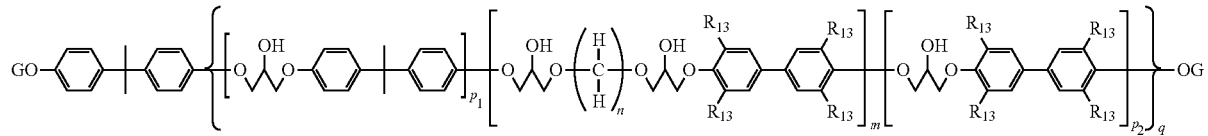
(A-12)

(A-13)

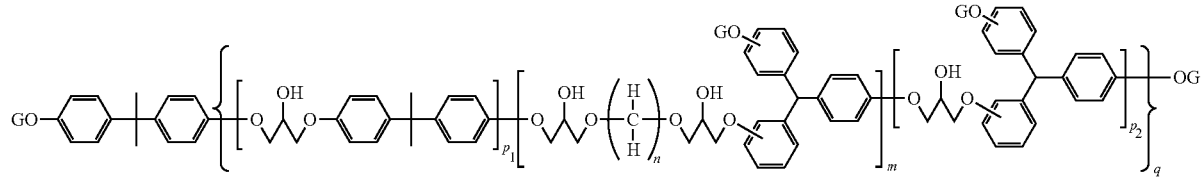

In each of the above structural formulae, G is a glycidyl group, $R_{13}$ is a hydrogen atom and/or a methyl group, n is an integer of 11 to 16, m, $p_1$, $p_2$, and q are average values of repetition, m is 0.5 to 10, $p_1$ and $p_2$ are each independently 0 to 5, and q is 0.5 to 5.

Among the above-mentioned structural formulae, those represented by the above-mentioned structural formulae (A-1), (A-2), (A-3), (A-5), (A-8), (A-9), and (A-10) are most preferably used from the viewpoint of excellent physical property balance of the obtained cured product.

<Production Method of Epoxy Compound A>

The method for producing the epoxy compound A of the present invention is not particularly limited, but it is preferable to use, for example, a method in which a hydroxy compound B obtained by reacting a diglycidyl ether of an aliphatic dihydroxy compound (a1) with an aromatic hydroxy compound (a2) in a molar ratio (a1)/(a2) of 1/1.01 to 1/5.0 is further reacted with an epihalohydrin (a3) from the viewpoints of easy availability of raw materials and easy reaction.

<Hydroxy Compound B>

When the epoxy compound A is obtained by reacting the diglycidyl ether of an aliphatic dihydroxy compound (a1) with the aromatic hydroxy compound (a2) to obtain a hydroxy compound B and further reacting the hydroxy compound B with the epihalohydrin (a3), the hydroxy compound B can be obtained by reacting the diglycidyl ether of an aliphatic dihydroxy compound (a1) with the aromatic hydroxy compound (a2) in a molar ratio (a1)/(a2) of 1/1.01 to 1/5.0.

Although the hydroxy compound B contains the unreacted aromatic hydroxy compound (a2), it may be used as it is in the present invention, or may be used after removing the aromatic hydroxy compound (a2).

The unreacted aromatic hydroxy compound (a2) can be removed by various methods. Examples thereof include a column chromatography separation method utilizing a difference in polarity, a distillation fractionation method utilizing a difference in boiling point, and an alkaline aqueous solution extraction method utilizing a difference in solubility in alkaline water. Among them, an alkaline aqueous solution extraction method is preferable in view of efficiency and the like because it is not accompanied by thermal deterioration, and at this time, an organic solvent which is not mixed with water, such as toluene or methyl isobutyl ketone, can be used as the organic solvent used for dissolving the target substance, but methyl isobutyl ketone is preferable from the viewpoint of solubility with the target substance. The content of the unreacted aromatic hydroxy compound (a2) in the obtained hydroxy compound B is preferably 0.1 to 30% by mass from the viewpoint of achieving a good balance between toughness and flexibility of the cured product.

The diglycidyl ether (a1) of an aliphatic dihydroxy compound is not particularly limited, and examples thereof include 1,11-undecanediol diglycidyl ether, 1,12-dodecanediol diglycidyl ether, 1,13-tridecanediol diglycidyl ether, 1,14-tetradecanediol diglycidyl ether, 1,15-pentadecanediol diglycidyl ether, 1,16-hexadecanediol diglycidyl ether, 2-methyl-1,11-undecanediol diglycidyl ether, 3-methyl-1,11-undecanediol diglycidyl ether, and 2,6,10-trimethyl-1,11-undecanediol diglycidyl ether. These may contain organic chlorine impurities produced in glycidyl etherification of hydroxy compounds, and may contain organic chlorine such as 1-chloromethyl-2-glycidyl ether (chloromethyl form) represented by the following structure. These diglycidyl ethers may be used alone or in combination of two or more kinds thereof.

[Chem. 8]

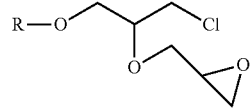

Chloromethyl Form

Among these, a compound having a structure in which a glycidyl group is linked to both ends of an alkylene chain having 12 to 14 carbon atoms via an ether group is preferable from the viewpoint of excellent balance between flexibility and heat resistance of the obtained cured product, and 1,12-dodecanediol diglycidyl ether, 1,13-tridecanediol diglycidyl ether, and 1,14-tetradecanediol diglycidyl ether are most preferably used.

The aromatic hydroxy compound (a2) is not particularly limited, and examples thereof include dihydroxybenzenes such as hydroquinone, resorcin, and catechol; trihydroxybenzenes such as pyrogallol, 1,2,4-trihydroxybenzene, and 1,3,5-trihydroxybenzene; triphenylmethane type phenols such as 4,4',4''-trihydroxytriphenylmethane; dihydroxynaphthalenes such as 1,6-dihydroxynaphthalene, 2,7-dihydroxynaphthalene, 1,4-dihydroxynaphthalene, 1,5-dihydroxynaphthalene, 2,3-dihydroxynaphthalene, and 2,6-dihydroxynaphthalene; tetrafunctional phenols such as 1,1'-methylenebis-(2,7-naphthalenediol), 1,1'-binaphthalene-2,2',7,7'-tetraol, and 1,1'-oxybis-(2,7-naphthalenediol), which are obtained by coupling dihydroxynaphthalenes; bisphenols such as bis(4-hydroxyphenyl)methane, 2,2-bis(4-hydroxyphenyl)propane, 2,2-bis(3-methyl-4-hydroxyphenyl) propane, 1,1-bis(4-hydroxyphenyl)cyclohexane, 1,1-bis(4-hydroxyphenyl)-1-phenylethane, and bis(4-hydroxyphenyl) sulfone; biphenols such as 2,2'-biphenol, 4,4'-biphenol, (1,1'-biphenyl)-3,4-diol, 3,3'-dimethyl-(1,1'-biphenyl)-4,4'-diol, 3-methyl-(1,1'-biphenyl)-4,4'-diol, 3,3',5,5'-tetramethylbiphenyl-2,2'-diol, 3,3',5,5'-tetramethylbiphenyl-4,4'-diol, 5-methyl-(1,1'-biphenyl)-3,4'-diol, 3'-methyl-(1,1'-biphenyl)-3,4'-diol, and 4'-methyl-(1,1'-biphenyl)-3,4'-diol; alicyclic structure-containing phenols such as a polyadduct of phenol and dicyclopentadiene and a polyadduct of phenol and a terpene-based compound; naphthols such as bis(2-hydroxy-1-naphthyl)methane and bis(2-hydroxy-1-naphthyl)propane; and a so-called Zylock-type phenol resin which is a condensation reaction product of phenol and phenylene dimethyl chloride or biphenylene dimethyl chloride, and these may be used alone or in combination of two or more kinds thereof. Further, a bifunctional phenol compound having a structure in which a methyl group, a t-butyl group, or a halogen atom is substituted as a substituent on the aromatic nucleus of each of the above-described compounds is also included. The alicyclic structure-containing phenol and the Zylock-type phenol resin may contain not only bifunctional components but also trifunctional or higher functional components at the same time. In the present invention, the alicyclic structure-containing phenol and the Zylock-type phenol resin may be used as they are, or only bifunctional components may be extracted and used through a purification step such as a column.

Among them, bisphenols are preferable from the viewpoint of excellent balance between flexibility and toughness when formed into a cured product, and bis(4-hydroxyphenyl)methane and 2,2-bis(4-hydroxyphenyl)propane are particularly preferable from the viewpoint of remarkable toughness imparting performance. When the moisture resistance of the cured product is important, phenols having an alicyclic structure are preferably used.

The reaction ratio of the diglycidyl ether of an aliphatic dihydroxy compound (a1) to the aromatic hydroxy compound (a2) is such that (a1)/(a2) must be in the range of 1/1.01 to 1/5.0 (molar ratio) in order to use the obtained compound as a curing agent for an epoxy resin, and (a1)/(a2) is preferably 1/1.1 to 1/3.0 (molar ratio) from the viewpoint of achieving a good balance between flexibility and heat resistance of the obtained cured product.

The reaction of the diglycidyl ether (a1) of an aliphatic dihydroxy compound with the aromatic hydroxy compound (a2) is preferably carried out in the presence of a catalyst. As the catalyst, various catalysts can be used, and examples thereof include alkali (earth)metal hydroxides such as sodium hydroxide, potassium hydroxide, lithium hydroxide, and calcium hydroxide; alkali metal carbonates such as sodium carbonate and potassium carbonate; phosphorus-based compounds such as triphenylphosphine; DMP-30; DMAP; chlorides, bromides, and iodides of tetramethylammonium, tetraethylammonium, tetrabutylammonium, and benzyltributylammonium; tetraammonium salts of chlorides, bromides, and iodides of tetramethylphosphonium, tetraethylphosphonium, tetrabutylphosphonium, and benzyltributylphosphonium; tertiary amines such as triethylamine, N,N-dimethylbenzylamine, 1,8-diazabicyclo[5.4.0]undecene, and 1,4-diazabicyclo[2.2.2]octane; and imidazoles such as 2-ethyl-4-methylimidazole and 2-phenylimidazole. These catalysts may be used in combination of two or more kinds. Among them, sodium hydroxide, potassium hydroxide, triphenylphosphine, and DMP-30 are preferable because the reaction proceeds rapidly and the effect of reducing the amount of impurities is high. The amount of the catalyst to be used is not particularly limited, but is preferably 0.0001 to 0.01 mol per 1 mol of the phenolic hydroxy group of the aromatic hydroxy compound (a2). The form of the catalyst also is not particularly limited, and the catalyst may be used in the form of an aqueous solution or a solid.

In addition, the reaction of the diglycidyl ether (a1) of an aliphatic dihydroxy compound with the aromatic hydroxy compound (a2) can be carried out in the absence of a solvent or in the presence of an organic solvent. Examples of usable organic solvents include methyl cellosolve, ethyl cellosolve, toluene, xylene, methyl isobutyl ketone, dimethyl sulfoxide, propyl alcohol, and butyl alcohol. The amount of the organic solvent to be used is usually 50 to 300% by mass, preferably 100 to 250% by mass, based on the total mass of the raw materials charged. These organic solvents may be used alone or in combination of several kinds thereof. In order to carry out the reaction rapidly, it is preferable to use no solvent, and on the other hand, from the viewpoint of reducing impurities in the final product, it is preferable to use dimethyl sulfoxide.

When the reaction is performed, the reaction temperature is usually 50 to 180° C., and the reaction time is usually 1 to 10 hours. The reaction temperature is preferably 100 to 160° C. from the viewpoint of reducing impurities in the final product. When the obtained compound is highly colored, an antioxidant or a reducing agent may be added to suppress the coloring. The antioxidant is not particularly limited, and examples thereof include hindered phenol compounds such as 2,6-dialkylphenol derivatives, divalent sulfur compounds, and trivalent phosphorus atom-containing phosphite compounds. The reducing agent is not particularly limited, and examples thereof include hypophosphorous acid, phosphorous acid, thiosulfuric acid, sulfurous acid, hydrosulfite, and salts thereof.

After completion of the reaction, the reaction mixture may be neutralized or washed with water until the pH value of the reaction mixture becomes 3 to 7, preferably 5 to 7. The neutralization treatment and water washing treatment may be carried out according to a conventional method. For example, when a basic catalyst is used, an acidic substance such as hydrochloric acid, sodium dihydrogen phosphate monobasic, p-toluenesulfonic acid or oxalic acid can be used as a neutralizing agent. After the neutralization or water washing treatment, if necessary, the solvent is distilled off under heating under reduced pressure and the product is concentrated to obtain the compound.

Preferred structures of the hydroxy compound B include the following structures.

[Chem. 9]

(b-1)

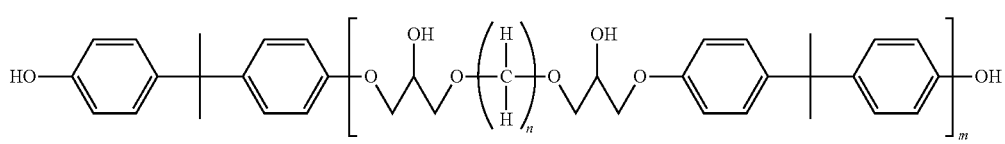

-continued
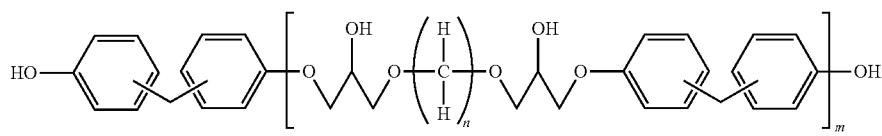
(b-2)
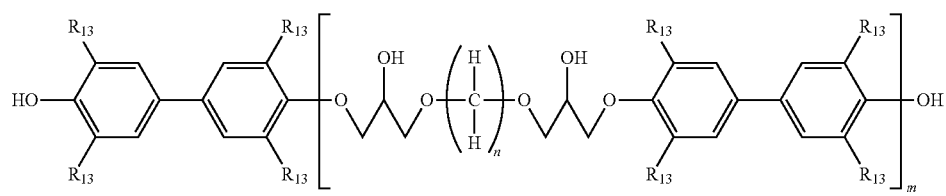
(b-3)
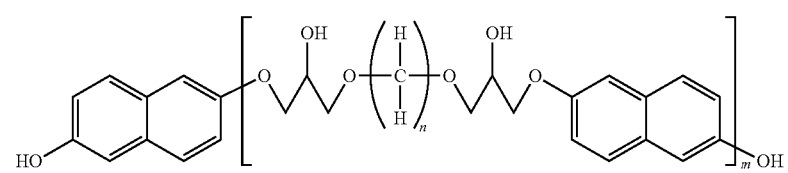
(b-4)
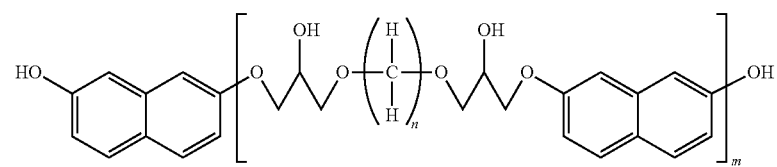
(b-5)
[Chem. 10]
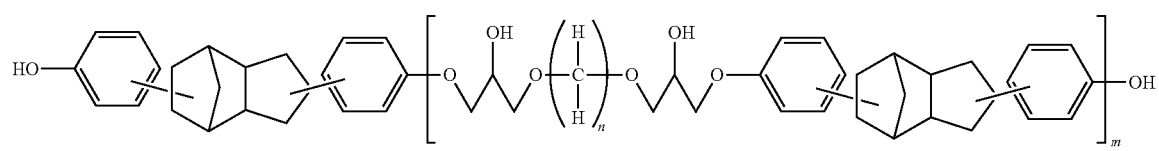
(b-6)
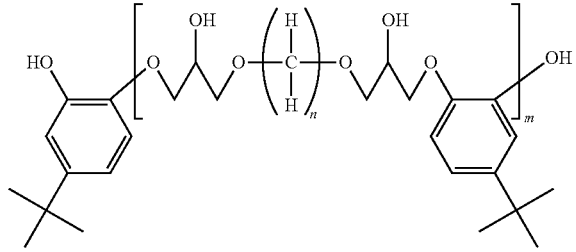
(b-7)
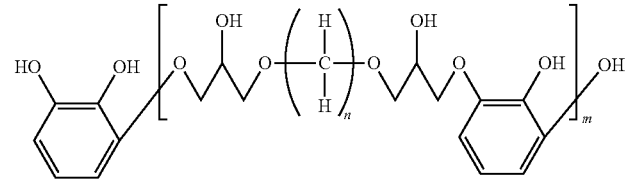
(b-8)
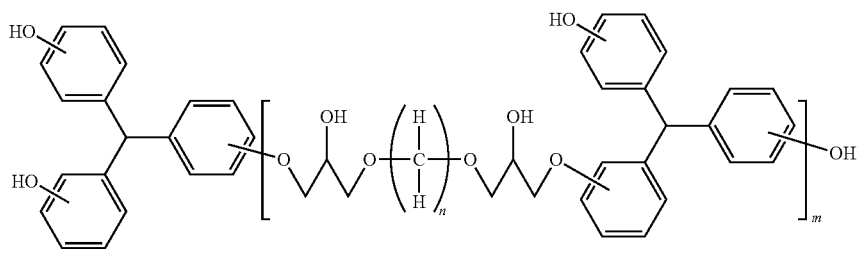
(b-9)

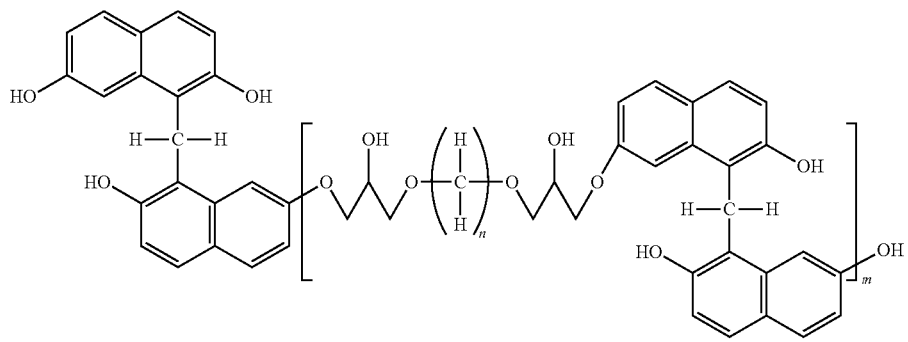
(b-10)

[Chem. 11]

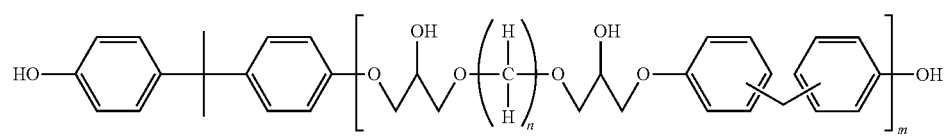
(b-11)

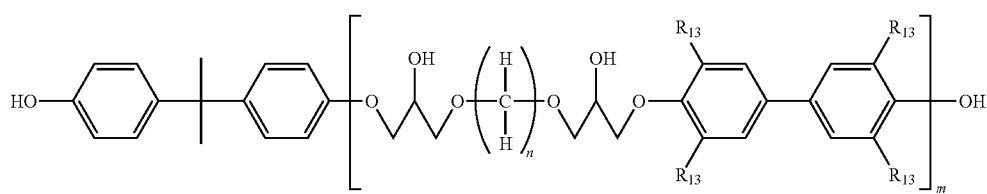
(b-12)

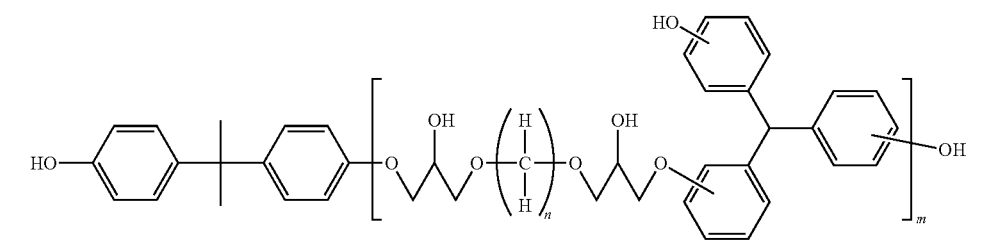
(b-13)

In each of the above structural formulae, $R_{13}$ is a hydrogen atom and/or a methyl group, n is an integer of 11 to 16, and m is an average value of repetition and is 0.5 to 10.

<Glycidyl Etherification Reaction>

In the method for producing the epoxy compound A of the present invention, the method of glycidyl etherification reaction of the hydroxy compound B is not particularly limited, and examples thereof include a method of reacting a phenolic hydroxy group with an epihalohydrin, and a method of olefinating a phenolic hydroxy group and oxidizing a carbon-carbon double bond of an olefin with an oxidizing agent. Among them, the method using an epihalohydrin is preferred from the viewpoints of easy availability of raw materials and easy reaction.

Examples of the method of using the epihalohydrin (a3) include a method of adding 0.3 to 20 mol of the epihalohydrin (a3) to 1 mol of the phenolic hydroxy group of the hydroxy compound B obtained above, and reacting the mixture at a temperature of 20 to 120° C. for 0.5 to 10 hours while adding 0.9 to 2.0 mol of a basic catalyst to 1 mol of the phenolic hydroxy group of the hydroxy compound B at once or gradually. With respect to the amount of the epihalohydrin (a3) added, as the excess amount of the epihalohydrin (a3) increases, the obtained epoxy compound becomes closer to the theoretical structure, and the formation of a second hydroxy group generated by the reaction between an unreacted phenolic hydroxy group and an epoxy group can be suppressed. From such a viewpoint, the amount is preferably in the range of 2.5 to 20 equivalents. The basic catalyst may be a solid or an aqueous solution thereof, and when an aqueous solution is used, the basic catalyst may be continuously added, water and the epihalohydrin (a3) may be continuously distilled out from the reaction mixture under reduced pressure or under normal pressure, the water may be removed by further separation, and the epihalohydrin (a3) may be continuously returned to the reaction mixture.

When industrial production is carried out, all of the charged epihalohydrins (a3) are used fresh in the first batch of epoxy compound production, but it is preferable to use the epihalohydrin (a3) recovered from the crude reaction product in combination with fresh epihalohydrin (a3) corresponding to the amount consumed and lost in the reaction in the next and subsequent batches. At this time, the epihalohydrin (a3) to be used is not particularly limited, and examples thereof include epichlorohydrin and epibromohydrin. Among them, epichlorohydrin is preferable because it is easily available.

Further, the basic catalyst is not particularly limited, and examples thereof include alkaline earth metal hydroxides, alkali metal carbonates, and alkali metal hydroxides. In particular, from the viewpoint of excellent catalytic activity in the epoxy resin synthesis reaction, an alkali metal hydroxide is preferable, and examples thereof include sodium hydroxide and potassium hydroxide. In use, these alkali metal hydroxides may be used in the form of an aqueous solution of about 10 to 55% by mass or in the form of a solid.

Further, by using an organic solvent in combination, the reaction rate in the synthesis of the epoxy compound can be increased. Such organic solvents are not particularly limited, and examples thereof include ketones such as acetone and methyl ethyl ketone; alcohols such as methanol, ethanol, 1-propyl alcohol, isopropyl alcohol, 1-butanol, secondary butanol, and tertiary butanol; cellosolves such as methyl cellosolve and ethyl cellosolve; ethers such as tetrahydrofuran, 1,4-dioxane, 1,3-dioxane, and diethoxyethane; and aprotic polar solvents such as acetonitrile, dimethyl sulfoxide, and dimethylformamide. These organic solvents may be used alone or in combination of two or more kinds thereof for adjusting the polarity.

After the reaction product of the glycidylation reaction is washed with water, unreacted epihalohydrin (a3) and the organic solvent used in combination are distilled off by heating under reduced pressure. In addition, in order to obtain an epoxy compound having less hydrolyzable halogen, the obtained epoxy compound may be dissolved again in an organic solvent such as toluene, methyl isobutyl ketone, or methyl ethyl ketone, and an aqueous solution of an alkali metal hydroxide such as sodium hydroxide or potassium hydroxide may be added to further carry out the reaction. At this time, a phase transfer catalyst such as a quaternary ammonium salt or a crown ether may be present for the purpose of improving the reaction rate.

When a phase transfer catalyst is used, the amount thereof is preferably in the range of 0.1 to 3.0% by mass with respect to the epoxy resin used. After completion of the reaction, the formed salt is removed by filtration, washing with water or the like, and the solvent such as toluene, methyl isobutyl ketone or the like is distilled off under heating and reduced pressure, whereby a high-purity epoxy compound can be obtained.

<Composition>

The composition of the present invention contains the epoxy compound A of the present invention.

The composition may contain components other than the epoxy compound A. For example, it is preferable to contain a curing agent capable of reacting with an epoxy compound.

The curing agent is not particularly limited as long as it can react with the epoxy compound, and examples thereof include amine compounds, acid anhydride compounds, amide compounds, phenol compounds, carboxylic acid compounds, and the hydroxy compound B described above.

Examples of the amine compound include aliphatic polyamines such as ethylenediamine, propylenediamine, butylenediamine, hexamethylenediamine, polypropyleneglycol diamine, diethylenetriamine, triethylenetetramine, and pentaethylenehexamine; aromatic polyamines such as metaxylylenediamine, diaminodiphenylmethane, and phenylenediamine; alicyclic polyamines such as 1,3-bis(aminomethyl) cyclohexane, isophorone diamine, and norbornane diamine; and dicyandiamide.

Examples of the acid anhydride compound include phthalic anhydride, trimellitic anhydride, pyromellitic anhydride, maleic anhydride, maleic anhydride polypropylene glycol, tetrahydrophthalic anhydride, methyltetrahydrophthalic anhydride, methylnadic anhydride, hexahydrophthalic anhydride, and methylhexahydrophthalic anhydride.

Examples of the phenolic compound include phenol novolac resin, cresol novolac resin, aromatic hydrocarbon formaldehyde resin-modified phenol resin, dicyclopentadiene phenol addition-type resin, phenol aralkyl resin, naphthol aralkyl resin, triphenylolmethane resin, tetraphenylolethane resin, naphthol novolac resin, naphthol-phenol co-condensed novolac resin, naphthol-cresol co-condensed novolac resin, biphenyl-modified phenol resin, aminotriazine-modified phenol resin, and modified products thereof. In addition, examples of the latent catalyst include imidazole, BF3-amine complexes, and guanidine derivatives.

Examples of the amide compound include an aliphatic polyamide synthesized from a polycarboxylic acid and a polyamine, an aromatic polyamide obtained by introducing an aromatic ring into the aliphatic polyamide, an aliphatic polyamide adduct obtained by adding an epoxy compound to a polyamide, and an aromatic polyamide adduct.

Examples of the carboxylic acid compound include carboxylic acid polymers such as carboxylic acid-terminated polyester, polyacrylic acid, and maleic acid-modified polypropylene glycol.

When these curing agents are used, only one curing agent may be used, or two or more curing agents may be mixed. In the application for an underfill material or a general coating material, it is preferable to use the amine compound, the carboxylic acid compound, and/or the acid anhydride compound. In addition, in the application for an adhesive or a flexible wiring board, an amine compound, particularly dicyandiamide is preferable from the viewpoints of workability, curability, and long-term stability. In addition, in the application for a semiconductor encapsulating material, a solid type phenolic compound is preferable from the viewpoint of heat resistance of a cured product.

<Other Epoxy Compounds>

In the composition of the present invention, in addition to the epoxy compound A, other epoxy compounds may be used in combination as long as the effects of the present invention are not impaired. At this time, the proportion of the epoxy compound A used in the composition of the present invention is preferably 30% by mass or more, particularly preferably 40% by mass or more, based on the total epoxy compounds.

Examples of the epoxy compound that can be used in combination include, but are not limited to, liquid epoxy resins such as a bisphenol A-type epoxy resin, a bisphenol F-type epoxy resin, a bisphenol S-type epoxy resin, a bisphenol AD-type epoxy resin, a resorcin-type epoxy resin, a hydroquinone-type epoxy resin, a catechol-type epoxy resin, a dihydroxynaphthalene-type epoxy resin, a biphenyl-type epoxy resin, and a tetramethylbiphenyl-type epoxy resin; brominated epoxy resins such as a brominated phenol novolac-type epoxy resin; a solid bisphenol A-type epoxy resin; a phenol novolac-type epoxy resin; a cresol novolac-type epoxy resin; a triphenylmethane-type epoxy resin; a tetraphenylethane-type epoxy resin; a dicyclopentadiene-phenol addition reaction-type epoxy resin; a phenol aralkyl-type epoxy resin; a phenylene ether-type epoxy resin; a naphthylene ether-type epoxy resin; a naphthol novolac-type epoxy resin; a naphthol aralkyl-type epoxy resin; a naphthol-phenol co-condensed novolac-type epoxy resin; a naphthol-cresol co-condensed novolac-type epoxy resin; an aromatic hydrocarbon formaldehyde resin-modified phenol resin-type epoxy resin; and a biphenyl-modified novolac-type epoxy resin. These epoxy compounds may be used alone or in combination of two or more kinds thereof, and it is preferable to select and use them in various ways depending on the intended use, physical properties of the cured product, and the like.

The blending amount of the epoxy compound and the curing agent in the composition of the present invention is not particularly limited, but from the viewpoint of good mechanical properties and the like of the obtained cured product, it is preferable that the amount of the active group in the curing agent is 0.7 to 1.5 equivalents with respect to 1 equivalent in total of the epoxy groups in the total amount of the epoxy compounds including the epoxy compound A.

<Curing Accelerator>

For example, the composition of the present invention may contain a curing accelerator. As the curing accelerator, various types may be used. Examples of the curing accelerator include urea compounds, phosphorus compounds, tertiary amines, imidazoles, organic acid metal salts, Lewis acids, and amine complex salts. When used as an adhesive, a urea compound, in particular, 3-(3,4-dichlorophenyl)-1,1-dimethylurea (DCMU) is preferable from the viewpoint of excellent workability and low-temperature curability. When used as a semiconductor encapsulating material, triphenylphosphine is preferable as the phosphorus compound and 1,8-diazabicyclo[5.4.0]undecene is preferable as the tertiary amine from the viewpoint of excellent curability, heat resistance, electrical characteristics, moisture resistance reliability, and the like.

<Filler>

The composition of the present invention may further contain a filler. Examples of the filler include an inorganic filler and an organic filler. Examples of the inorganic filler include inorganic fine particles.

Examples of the inorganic fine particles include those having excellent heat resistance, such as alumina, magnesia, titania, zirconia, and silica (quartz, fumed silica, precipitated silica, silicic anhydride, fused silica, crystalline silica, ultra-fine amorphous silica, and the like); those having excellent heat conductivity, such as boron nitride, aluminum nitride, alumina oxide, titanium oxide, magnesium oxide, zinc oxide, silicon oxide, and diamond; those having excellent conductivity, such as metal fillers and/or metal-coated fillers using a metal single body or an alloy (for example, iron, copper, magnesium, aluminum, gold, silver, platinum, zinc, manganese, stainless steel, etc.); those having excellent barrier properties, such as minerals such as mica, clay, kaolin, talc, zeolite, wollastonite, and smectite, potassium titanate, magnesium sulfate, sepiolite, xonotlite, aluminum borate, calcium carbonate, titanium oxide, barium sulfate, zinc oxide, and magnesium hydroxide; those having a high refractive index, such as barium titanate, zirconia oxide, and titanium oxide; those having photocatalytic properties, such as titanium, cerium, zinc, copper, aluminum, tin, indium, phosphorus, carbon, sulfur, tellurium, nickel, iron, cobalt, silver, molybdenum, strontium, chromium, barium, and lead, composites of these metals, and oxides thereof; those having excellent abrasion resistance, such as metals such as silica, alumina, zirconia, and magnesium oxide, and composites and oxides thereof; those having excellent conductivity, such as metals such as silver and copper, tin oxide, and indium oxide; those having excellent insulation, such as silica; and those having excellent ultraviolet shielding, such as titanium oxide and zinc oxide.

These inorganic fine particles may be appropriately selected depending on the application, and may be used alone or in combination of two or more kinds thereof. In addition, since the inorganic fine particles have various properties in addition to the properties exemplified above, the inorganic fine particles may be appropriately selected according to the intended use.

For example, when silica is used as the inorganic fine particles, known silica fine particles such as powdery silica and colloidal silica can be used without particular limitation. Examples of commercially available powdery silica fine particles include Aerosil 50 and 200 manufactured by Nippon Aerosil Co., Ltd., Sildex H31, H32, H51, H52, H121, and H122 manufactured by Asahi Glass Co., Ltd., E220A and E220 manufactured by Nippon Silica Industry Co., Ltd., SYLYSIA470 manufactured by Fuji Silysia Chemical Ltd., and SG Flake manufactured by Nippon Sheet Glass Co., Ltd.

Examples of commercially available colloidal silica include methanol silica sol, IPA-ST, MEK-ST, NBA-ST, XBA-ST, DMAC-ST, ST-UP, ST-OUP, ST-20, ST-40, ST-C, ST-N, ST-O, ST-50, and ST-OL manufactured by Nissan Chemical Industries, Ltd.

Surface-modified silica fine particles may be used, and examples thereof include silica fine particles surface-treated with a reactive silane coupling agent having a hydrophobic group, and silica fine particles modified with a compound having a (meth)acryloyl group. Examples of commercially available powdery silica modified with a compound having a (meth)acryloyl group include Aerosil RM50 and R711 manufactured by Nippon Aerosil Co., Ltd., and examples of commercially available colloidal silica modified with a compound having a (meth)acryloyl group include MIBK-SD manufactured by Nissan Chemical Industries, Ltd.

The shape of the silica fine particles is not particularly limited, and spherical, hollow, porous, rod-like, plate-like, fibrous, or amorphous silica fine particles can be used. The primary particle size is preferably in the range of 5 to 200 nm. If it is less than 5 nm, the dispersion of the inorganic fine particles in the dispersion becomes insufficient, and if it exceeds 200 nm, the strength of the cured product may not be sufficiently maintained.

As the titanium oxide fine particles, not only an extender pigment but also an ultraviolet light-responsive photocatalyst can be used, and for example, anatase type titanium oxide, rutile type titanium oxide, brookite type titanium oxide and the like can be used. Further, particles designed to respond to visible light by doping a different element into the crystal structure of titanium oxide can also be used. As the element with which titanium oxide is doped, an anion element such as nitrogen, sulfur, carbon, fluorine, or phosphorus, or a cation element such as chromium, iron, cobalt, or manganese is preferably used. As the form, a powder form, or a sol or slurry form dispersed in an organic solvent or water can be used. Examples of commercially available powdery titanium oxide fine particles include Aerosil P-25 manufactured by Nippon Aerosil Co., Ltd. and ATM-100 manufactured by Tayca Corporation. Examples of commercially available slurry-like titanium oxide fine particles include TKD-701 manufactured by Tayca Corporation.

<Fibrous Substrate>

The composition of the present invention may further contain a fibrous substrate. The fibrous substrate of the present invention is not particularly limited, but is preferably used for a fiber-reinforced resin, and examples thereof include inorganic fibers and organic fibers.

Examples of the inorganic fibers include carbon fibers, activated carbon fibers, graphite fibers, glass fibers, tungsten carbide fibers, silicon carbide fibers (silicon carbide fibers), ceramic fibers, alumina fibers, natural fibers, mineral fibers such as basalt, boron fibers, boron nitride fibers, boron carbide fibers, and metal fibers, in addition to inorganic fibers such as carbon fibers, glass fibers, boron fibers, alumina fibers, and silicon carbide fibers. Examples of the metal fibers include aluminum fibers, copper fibers, brass fibers, stainless steel fibers, and steel fibers.

Examples of the organic fibers include synthetic fibers made of resin materials such as polybenzazole, aramid, PBO (polyparaphenylene benzoxazole), polyphenylene sulfide, polyester, acrylic, polyamide, polyolefin, polyvinyl alcohol, and polyarylate; natural fibers such as cellulose, pulp, cotton, wool, and silk; and regenerated fibers such as protein, polypeptide, and alginic acid.

Among them, carbon fibers and glass fibers are preferable because they have a wide industrial application range. Of these, only one kind may be used, and a plurality of kinds may be used simultaneously.

The fibrous substrate of the present invention may be an aggregate of fibers, and the fibers may be continuous or discontinuous, and may be woven or nonwoven. In addition, a fiber bundle in which fibers are aligned in one direction may be used, or a sheet in which fiber bundles are arranged may be used. In addition, the fiber aggregate may have a three dimensional shape having a thickness.

<Dispersion Medium>

In the composition of the present invention, a dispersion medium may be used for the purpose of adjusting the solid content or viscosity of the composition. The dispersion medium may be any liquid medium that does not impair the effects of the present invention, and examples thereof include various organic solvents and liquid organic polymers.

Examples of the organic solvent include ketones such as acetone, methyl ethyl ketone (MEK), and methyl isobutyl ketone (MIBK); cyclic ethers such as tetrahydrofuran (THF) and dioxolane; esters such as methyl acetate, ethyl acetate, and butyl acetate; aromatics such as toluene and xylene; and alcohols such as carbitol, cellosolve, methanol, isopropanol, butanol, and propylene glycol monomethyl ether, which can be used alone or in combination. Among them, methyl ethyl ketone is preferable from the viewpoints of volatility at the time of coating and solvent recovery.

The liquid organic polymer is a liquid organic polymer that does not directly contribute to the curing reaction, and examples thereof include a carboxyl group-containing polymer modified product (Flowlen G-900, NC-500: Kyoeisha Chemical Co., Ltd.), an acrylic polymer (Flowlen WK-20: Kyoeisha Chemical Co., Ltd.), amine salts of a specially modified phosphoric acid ester (HIPLAAD ED-251: Kusumoto Chemicals, Ltd.), and a modified acrylic block copolymer (DISPERBYK2000: BYK Japan KK).

<Resin>

The composition of the present invention may contain a resin other than the above-mentioned various compounds of the present invention. As the resin, a known and commonly used resin may be blended as long as the effects of the present invention are not impaired, and for example, a thermosetting resin or a thermoplastic resin can be used.

The thermosetting resin is a resin having a property capable of being changed into substantially insoluble and infusible when cured by means of heating, radiation, a catalyst or the like. Specific examples of the thermosetting resin include phenol resins, urea resins, melamine resins, benzoguanamine resins, alkyd resins, unsaturated polyester resins, vinyl ester resins, diallyl terephthalate resins, silicone resins, urethane resins, furan resins, ketone resins, xylene resins, thermosetting polyimide resins, benzoxazine resins, active ester resins, aniline resins, cyanate ester resins, styrene-maleic anhydride (SMA) resins, and maleimide resins.

These thermosetting resins may be used alone or in combination of two or more kinds thereof.

The thermoplastic resin refers to a resin that can be melt-molded by heating. Specific examples of the thermoplastic resin include polyethylene resins, polypropylene resins, polystyrene resins, rubber-modified polystyrene resins, acrylonitrile-butadiene-styrene (ABS) resins, acrylonitrile-styrene (AS) resins, polymethyl methacrylate resins, acrylic resins, polyvinyl chloride resins, polyvinylidene chloride resins, polyethylene terephthalate resins, ethylene vinyl alcohol resins, cellulose acetate resins, ionomer resins, polyacrylonitrile resins, polyamide resins, polyacetal resins, polybutylene terephthalate resins, polylactic acid resins, polyphenylene ether resins, modified polyphenylene ether resins, polycarbonate resins, polysulfone resins, polyphenylene sulfide resins, polyetherimide resins, polyethersulfone resins, polyarylate resins, thermoplastic polyimide resins, polyamideimide resins, polyether ether ketone resins, polyketone resins, liquid crystal polyester resins, fluororesins, syndiotactic polystyrene resins, and cyclic polyolefin resins. These thermoplastic resins may be used alone or in combination of two or more kinds thereof.

<Other Formulations>

The composition of the present invention may have other formulations. Examples thereof include catalysts, polymerization initiators, inorganic pigments, organic pigments, extender pigments, clay minerals, waxes, surfactants, stabilizers, flow control agents, coupling agents, dyes, leveling agents, rheology control agents, ultraviolet absorbers, antioxidants, flame retardants, plasticizers, and reactive diluents.

<Cured Product>

In the composition of the present invention, by applying a reaction product of a diglycidyl ether of an aliphatic dihydroxy compound and an aromatic hydroxy compound, it is possible to obtain a flexible and tough cured product which has not been obtained conventionally. For example, a high molecular weight epoxy compound obtained by reacting the above-mentioned liquid bisphenol A type epoxy resin with an aliphatic dicarboxylic acid such as dimer acid or sebacic acid as a molecular chain extender gives a cured product having a flexible structure, but its effect is not sufficient due to aggregation of ester groups.

In contrast, in the present invention, since the skeleton formed from the aliphatic compound functions as a so-called soft segment that imparts flexibility, the cured product obtained by curing the epoxy compound A of the present invention is extremely flexible. On the other hand, since the skeleton formed from the aromatic hydroxy compound functions as a so-called hard segment that imparts rigidity to the epoxy compound A of the present invention, a cured product having both flexibility and toughness can be provided.

In particular, in the case of the epoxy compound A of the present invention, a portion functioning as a hard segment and a portion functioning as a soft segment are bonded to each other, whereby flexibility can be imparted to the epoxy compound structure and excellent moisture resistance can be exhibited. Further, in the present invention, the glycidyloxy group is directly bonded to the aromatic nucleus, whereby the toughness of the epoxy cured product becomes extremely excellent. That is, for example, a general-purpose epoxy resin having a structure in which a diol compound obtained by modifying a liquid bisphenol A type epoxy resin of a low content type with ethylene oxide or propylene oxide is glycidyl-etherified has a flexible epoxy resin skeleton itself, but is inferior in the activity of an epoxy group itself and cannot obtain sufficient crosslinking for exhibiting toughness during curing. However, in the epoxy compound A of the present invention, since the glycidyloxy group is directly bonded to the aromatic nucleus, the activity of the epoxy group is increased, and therefore, although the resin itself is flexible, appropriate crosslinking is formed during the curing reaction, and excellent toughness is exhibited. Furthermore, since the hard segment is adjacent to an epoxy group serving as a crosslinking point, physical strength at the crosslinking point is increased and toughness is improved.

When the composition of the present invention is cured, it may be cured at room temperature or by heating. Upon curing, a known and commonly used curing catalyst may be used.

In the case of performing thermal curing, curing may be performed by one time of heating, or curing may be performed through a multi-stage heating step.

When a curing catalyst is used, for example, inorganic acids such as hydrochloric acid, sulfuric acid, and phosphoric acid; organic acids such as p-toluenesulfonic acid, monoisopropyl phosphate, and acetic acid; inorganic bases such as sodium hydroxide and potassium hydroxide; titanates such as tetraisopropyl titanate and tetrabutyl titanate; compounds containing various basic nitrogen atoms, such as 1,8-diazabicyclo[5.4.0]undecene-7 (DBU), 1,5-diazabicyclo[4.3.0]nonene-5 (DBN), 1,4-diazabicyclo[2.2.2]octane (DABCO), tri-n-butylamine, dimethylbenzylamine, monoethanolamine, imidazole, 2-ethyl-4-methyl-imidazole, 1-methylimidazole, and N,N-dimethyl-4-aminopyridine (DMAP); various quaternary ammonium salts such as a tetramethylammonium salt, a tetrabutylammonium salt, and a dilauryldimethylammonium salt, in which the quaternary ammonium salts have chloride, bromide, carboxylate, hydroxide, or the like as a counter anion; tin carboxylates such as dibutyltin diacetate, dibutyltin dioctoate, dibutyltin dilaurate, dibutyltin diacetylacetonate, tin octylate, or tin stearate; and organic peroxides such as benzoyl peroxide, cumene hydroperoxide, dicumyl peroxide, lauroyl peroxide, di-t-butyl peroxide, t-butyl hydroperoxide, methyl ethyl ketone peroxide, and t-butyl perbenzoate can be used. These catalysts may be used alone or in combination of two or more kinds thereof.

The composition of the present invention can also be cured with active energy rays. In this case, a photocationic polymerization initiator may be used as the polymerization initiator. As the active energy rays, visible rays, ultraviolet rays, X-rays, electron beams, and the like can be used.

Examples of the photocationic polymerization initiator include arylsulfonium salts and aryliodonium salts, and specific examples thereof include arylsulfonium hexafluorophosphate, arylsulfonium hexafluoroantimonate, arylsulfonium tetrakis(pentafluoro)borate, and tri(alkylphenyl) hexafluorophosphate. These photocationic polymerization initiators may be used alone or in combination of two or more kinds thereof.

<Laminate>

The cured product of the present invention can be laminated with a substrate to form a laminate.

As the substrate of the laminate, an inorganic material such as metal or glass, an organic material such as plastic or wood, or the like may be appropriately used depending on the application, and the shape of the laminate may be a flat plate, a sheet, a three dimensional structure, or may have a three dimensional shape. The shape may be any shape according to the purpose, such as a shape having a curvature on the entire surface or a part thereof. The hardness, thickness, and the like of the substrate are also not limited. In addition, the cured product of the present invention may be used as a substrate, and the cured product of the present invention may be further laminated.

The composition of the present invention has particularly high adhesiveness to metals and/or metal oxides, and thus can be particularly well used as a primer for metals. Examples of the metal include copper, aluminum, gold, silver, iron, platinum, chromium, nickel, tin, titanium, zinc, various alloys, and composite materials thereof, and examples of the metal oxide include single oxides and composite oxides of these metals. In particular, it is excellent in adhesive force to iron, copper, and aluminum, and thus can be favorably used as an adhesive for iron, copper, and aluminum.

In the laminate of the present invention, the cured product layer may be formed on the substrate by direct coating or molding, or may be formed by laminating an already molded product. In the case of direct coating, the coating method is not particularly limited, and examples thereof include a spray method, a spin coating method, a dip method, a roll coating method, a blade coating method, a doctor roll method, a doctor blade method, a curtain coating method, a slit coating method, a screen printing method, and an inkjet method. Examples of direct molding include in-mold molding, insert molding, vacuum molding, extrusion laminate molding, and press molding.

When the molded composition is laminated, an uncured or semi-cured composition layer may be laminated and then cured, or a cured product layer obtained by completely curing the composition may be laminated on the substrate.

In addition, the cured product of the present invention may be laminated by coating and curing a precursor that can serve as a substrate, or may be cured after the precursor that can serve as a substrate or the composition of the present invention is adhered in an uncured or semi-cured state. The precursor that can serve as a substrate is not particularly limited, and examples thereof include various curable resin compositions.

<Fiber-Reinforced Resin>

When the composition of the present invention has a fibrous substrate and the fibrous substrate is a reinforcing fiber, the composition containing the fibrous substrate can be used as a fiber-reinforced resin.

The method of incorporating the fibrous substrate into the composition is not particularly limited as long as the effects of the present invention are not impaired, and examples thereof include a method of compounding the fibrous substrate and the composition by a method such as kneading, coating, impregnation, injection, or pressure bonding, and the method can be appropriately selected depending on the form of the fiber and the application of the fiber-reinforced resin.

The method for molding the fiber-reinforced resin of the present invention is not particularly limited. When a plate-shaped product is produced, an extrusion molding method is generally used, but a flat press can also be used. In addition, an extrusion molding method, a blow molding method, a compression molding method, a vacuum molding method, an injection molding method, or the like can be used. When a film-like product is produced, a solution casting method can be used in addition to a melt extrusion method, and when the melt molding method is used, inflation film molding, cast molding, extrusion lamination molding, calender molding, sheet molding, fiber molding, blow molding, injection molding, rotational molding, coating molding, and the like can be exemplified. In addition, in the case of a resin curable with active energy rays, a cured product can be produced by various curing methods using active energy rays. In particular, when a thermosetting resin is used as a main component of a matrix resin, a molding method in which a molding material is formed into a prepreg and pressurized and heated by a press or an autoclave is exemplified, and in addition to this, RTM (Resin Transfer Molding) molding, VaRTM (Vacuum assist Resin Transfer Molding) molding, lamination molding, hand lay-up molding, and the like are exemplified.

<Prepreg>

The fiber-reinforced resin of the present invention can form a state called an uncured or semi-cured prepreg. The product may be distributed in the form of a prepreg and then subjected to final curing to form a cured product. In the case of forming a laminate, it is preferable to form a prepreg, then laminate other layers, and then perform final curing, because a laminate in which each layer is in close contact can be formed.

The mass ratio between the composition and the fibrous substrate used at this time is not particularly limited, but it is usually preferable to prepare the prepreg so that the resin content in the prepreg is 20 to 60% by mass.

<Heat-Resistant Materials and Electronic Materials>

Since the cured product of the composition of the present invention has a high glass transition temperature and excellent thermal decomposition resistance, the composition can be suitably used for heat-resistant members. In addition, since it has excellent adhesion to a substrate, it can be suitably used particularly for electronic members. In particular, the composition of the present invention can be suitably used for a semiconductor encapsulating material, a circuit board, a buildup film, a buildup substrate, an adhesive, or a resist material. In addition, it can be suitably used as a matrix resin of a fiber-reinforced resin, and is particularly suitable as a prepreg having high heat resistance. The heat-resistant member and the electronic member thus obtained can be suitably used for various applications, and examples thereof include, but are not limited to, industrial machine parts, general machine parts, parts such as automobiles, trains, and vehicles, space-related and aircraft-related parts, electronic and electrical parts, building materials, containers and packaging members, household goods, sports and leisure goods, and housing members for wind power generation.

Typical products are described below by way of example.

1. Semiconductor Encapsulating Material

Examples of the method for obtaining a semiconductor encapsulating material from the composition of the present invention include a method in which the composition, a curing accelerator, and a compounding agent such as an inorganic filler are sufficiently melt-mixed until the mixture becomes uniform using an extruder, a kneader, a roll, or the like as necessary. In this case, fused silica is usually used as the inorganic filler, but in the case of using the inorganic filler as a highly heat-conductive semiconductor encapsulating material for power transistors and power ICs, it is preferable to use crystalline silica, alumina, silicon nitride, or the like having higher thermal conductivity than fused silica in a high filling rate, or fused silica, crystalline silica, alumina, silicon nitride, or the like. The filling rate of the inorganic filler is preferably in the range of 30 to 95% by mass per 100 parts by mass of the curable resin composition. In particular, the filling rate is more preferably 70 parts by mass or more, and still more preferably 80 parts by mass or more, in order to improve flame retardancy, moisture resistance, and solder crack resistance, and decrease the linear expansion coefficient.

2. Semiconductor Device

Examples of the semiconductor package molding for obtaining a semiconductor device from the curable resin composition of the present invention include a method in which the semiconductor encapsulating material is cast or molded using a transfer molding machine, an injection molding machine, or the like, and further heated at 50 to 250° C. for 2 to 10 hours.

3. Printed Circuit Board

A printed circuit board can be obtained from the composition of the present invention by laminating the above-mentioned prepregs by a conventional method, appropriately laminating a copper foil, and performing press-bonding under heating at 170 to 300° C. for 10 minutes to 3 hours under a pressure of 1 to 10 MPa.

4. Buildup Substrate

Examples of a method for obtaining a buildup substrate from the composition of the present invention include the following steps. Step 1 is a step of first applying the above-described composition, in which rubber, filler, and the like are appropriately blended, to a circuit board on which a circuit is formed by a spray coating method, a curtain coating method, or the like, and then curing the composition. Step 2 is a step of drilling a predetermined through-hole portion or the like as necessary, then treating the through-hole portion or the like with a roughening agent, washing the surface of the through-hole portion or the like with hot water to form irregularities, and plating the surface with a metal such as copper. Step 3 is a step in which such an operation is sequentially repeated as desired to alternately build up and form a resin insulating layer and a conductor layer having a predetermined circuit pattern. Drilling of the through-hole portion is performed after formation of the outermost resin insulating layer. In addition, in the buildup substrate of the present invention, a resin-coated copper foil obtained by semi-curing the resin composition on a copper foil is press-bonded under heating at 170 to 300° C. on a wiring substrate on which a circuit is formed, whereby a buildup substrate can be produced without the steps of forming a roughened surface and plating treatment.

5. Buildup Film

As a method for obtaining a buildup film from the composition of the present invention, the buildup film can be produced by applying the composition to the surface of the support film (Y) as a substrate, and further drying the organic solvent by heating or blowing hot air to form the layer (X) of the composition.

As the organic solvent used herein, for example, ketones such as acetone, methyl ethyl ketone, and cyclohexanone, acetates such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethylformamide, dimethylacetamide, and N-methylpyrrolidone are preferably used, and the nonvolatile content is preferably 30 to 60% by mass.

The thickness of the layer (X) to be formed is usually not less than the thickness of the conductor layer. Since the thickness of the conductor layer of the circuit board is usually in the range of 5 to 70 μm, the thickness of the resin composition layer is preferably 10 to 100 μm. The layer (X) of the composition in the present invention may be protected by a protective film described later. By protecting the composition of the present invention with the protective film, it is possible to prevent adhesion of dust or scratches to the surface of the resin composition layer.

Examples of the support film and the protective film include polyolefins such as polyethylene, polypropylene, and polyvinyl chloride; polyesters such as polyethylene terephthalate (hereinafter sometimes abbreviated as "PET") and polyethylene naphthalate; polycarbonates; polyimides; and release paper and metal foils such as copper foil and aluminum foil. The support film and the protective film may be subjected to release treatment in addition to mud treatment and corona treatment. The thickness of the support film is not particularly limited, but is usually 10 to 150 μm, and preferably 25 to 50 μm. The thickness of the protective film is preferably 1 to 40 μm.

The above-mentioned support film (Y) is peeled off after laminating on a circuit board or after forming an insulating layer by heat curing. When the support film (Y) is peeled off after the curable resin composition layer constituting the buildup film is cured by heating, adhesion of dust or the like in the curing step can be prevented. In the case of peeling after curing, the support film is usually subjected to release treatment in advance.

A multilayer printed circuit board may be manufactured using the buildup film obtained as described above. For example, when the layer (X) is protected by a protective film, the protective film is peeled off, and then the layer (X) is laminated on one side or both sides of the circuit board so as to be in direct contact with the circuit board, for example, by a vacuum lamination method. The laminating method may be a batch method or a continuous method using rolls. If necessary, the buildup film and the circuit board may be heated (preheated) before lamination. As for the lamination conditions, the pressure bonding temperature (lamination temperature) is preferably 70 to 140° C., the pressure bonding pressure is preferably 1 to 11 kgf/cm$^2$ (9.8×10$^4$ to 107.9×10$^4$ N/m$^2$), and lamination is preferably performed under a reduced pressure of 20 mmHg (26.7 hPa) or less.

6. Conductive Paste

Examples of a method for obtaining a conductive paste from the composition of the present invention include a method in which conductive particles are dispersed in the composition. The conductive paste may be a paste resin composition for circuit connection or an anisotropic conductive adhesive depending on the type of conductive particles used.

EXAMPLES

Next, the present invention will be described in more detail with reference to Examples and Comparative Examples. Hereinafter, "parts" and "%" are based on mass unless otherwise specified.

$^1$H and $^{13}$C-NMR, FD-MS spectra, and GPC were measured under the following conditions.

$^1$H-NMR: "JNM-ECA600" manufactured by JEOL RESONANCE Inc.
  Magnetic field strength: 600 MHz
  Number of integration: 32 times
  Solvent: DMSO-d$_6$
  Sample concentration: 30% by mass
$^{13}$C-NMR: "JNM-ECA600" manufactured by JEOL RESONANCE Inc.
  Magnetic field strength: 150 MHz
  Number of integration: 320 times
  Solvent: DMSO-d$_6$
  Sample concentration: 30% by mass FD-MS: "JMS-T100GC AccuTOF" manufactured by JEOL Ltd.
  Measurement range: m/z=50.00 to 2000.00
  Rate of change: 25.6 mA/min
  Final current value: 40 mA
  Cathode voltage: −10 kV
GPC: "HLC-8320GPC" manufactured by Tosoh Corporation
  Column: "TSK-GEL G2000HXL"+"TSK-GEL G3000HXL"+"TSK-GEL G4000HXL" manufactured by Tosoh Corporation
  Detector: RI (Differential Refractometer)
  Measurement conditions: 40° C.
  Mobile phase: tetrahydrofuran
  Flow rate: 1 ml/min
  Standard: "PStQuick A", "PStQuick B", "PStQuick E", and "PStQuick F" manufactured by Tosoh Corporation The epoxy equivalents of the synthesized epoxy compounds were measured according to JIS K7236, and the epoxy equivalents (g/eq) were calculated.

Examples of the method for calculating the number of repeating units include GPC molecular weight measurement and calculation from various appropriate instrumental analysis results such as FD-MS and NMR.

Synthesis Example 1: Hydroxy Compound B-1 of C12 Type (BPA)

A flask equipped with a thermometer and a stirrer was charged with 210 g (0.5 mol) of diglycidyl ether of 1,12-dodecanediol (epoxy equivalent 210 g/eq, manufactured by Yokkaichi Chemical Co., Ltd.) and 228 g (1.0 mol) of bisphenol A (hydroxyl equivalent 114 g/eq), heated to 140° C. over 30 minutes, and then charged with 1 g of a 4% sodium hydroxide aqueous solution. Thereafter, the temperature was raised to 150° C. over 30 minutes, and the mixture was further reacted at 150° C. for 3 hours. Thereafter, a neutralizing amount of sodium phosphate was added to obtain 430 g of hydroxy compound B-1. The mass spectrum of this hydroxy compound B-1 was found to have a peak of M+=771. From this, it was found to contain the hydroxy compound having the structure represented by the structural formula (b-1). The hydroxyl equivalent of this hydroxy compound B-1 calculated by GPC was 330 g/eq, and the average value of m in the structural formula (b-1) was 0.8.

Synthesis Example 2: Hydroxy Compound B-2 of C12 Type (Pyrogallol 330 g of hydroxy compound B-2 was obtained by the same reaction as in Synthesis Example 1 except that 228 g (1.0 mol) of bisphenol A in Synthesis Example 1 was changed to 126 g (1.0 mol) of pyrogallol. The mass spectrum of this hydroxy compound B-2 was found to have a peak of M+=567. From this, it was found to contain the hydroxy compound having the structure represented by the structural formula (b-8). The hydroxyl equivalent of this hydroxy compound B-2 calculated by GPC was 121 g/eq, and the average value of m in the structural formula (b-8) was 0.8.

Synthesis Example 3: Hydroxy Compound B-3 of C12 Type (Biphenol and Tetramethylbiphenol in Combination 415 g of hydroxy compound B-3 was obtained by the same reaction as in Synthesis Example 1 except that 228 g (1.0 mol) of bisphenol A in Synthesis Example 1 was changed to 93 g (0.5 mol) of 4,4'-biphenol and 121 g (0.5 mol) of 3,3',5,5'-tetramethylbiphenyl-4,4'-diol. The mass spectrum of this hydroxy compound B-3 was observed to have peaks of M+=687, 744, and 800. From this, it was found to contain the hydroxy compound having the structure represented by the structural formula (b-3). The hydroxyl equivalent of this hydroxy compound B-3 calculated by GPC was 318 g/eq, and the average value of m in the structural formula (b-3) was 0.8.

Synthesis Example 4: Hydroxy Compound B-4 of C12 Type (Tetramethylbiphenol 458 g of hydroxy compound B-4 was obtained by the same reaction as in Synthesis Example 1 except that 228 g (1.0 mol) of bisphenol A in Synthesis Example 1 was changed to 242 g (1.0 mol) of 3,3',5,5'-tetramethylbiphenyl-4,4'-diol. The mass spectrum of this hydroxy compound B-4 was observed to have a peak of M+=800. From this, it was found to contain the hydroxy compound having the structure represented by the structural formula (b-3). The hydroxyl equivalent of this hydroxy compound B-4 calculated by GPC was 342 g/eq, and the average value of m in the structural formula (b-3) was 0.8.

Synthesis Example 5: Hydroxy Compound B-5 of C12 Type (2,7-Dihydroxynaphthalene 361 g of hydroxy compound B-5 was obtained by the same reaction as in Synthesis Example 1 except that 228 g (1.0 mol) of bisphenol A in Synthesis Example 1 was changed to 160 g (1.0 mol) of 2,7-dihydroxy naphthalene. The mass spectrum of this hydroxy compound B-5 was observed to have a peak of M+=635. From this, it was found to contain the hydroxy compound having the structure represented by the structural formula (b-5). The hydroxyl equivalent of this hydroxy compound B-5 calculated by GPC was 271 g/eq, and the average value of m in the structural formula (b-5) was 0.8.

Synthesis Example 6: Hydroxy Compound B-6 of C12 Type (Triphenylolmethane 498 g of hydroxy compound B-6 was obtained by the same reaction as in Synthesis Example 1 except that 228 g (1.0 mol) of bisphenol A in Synthesis Example 1 was changed to 292 g (1.0 mol) of triphenylolmethane ("TPM-100" manufactured by Gunei Chemical Industry Co., Ltd.). The mass spectrum of this hydroxy compound B-6 was observed to have a peak of M+=900. From this, it was found to contain the hydroxy compound having the structure represented by the structural formula (b-9). The hydroxyl equivalent of this hydroxy compound B-6 calculated by GPC was 192 g/eq, and the average value of m in the structural formula (b-9) was 0.8.

Synthesis Example 7: Hydroxy Compound B-7 of C12 Type (Bis-naphthalenediol 522 g of hydroxy compound B-7 was obtained by the same reaction as in Synthesis Example 1 except that 228 g (1.0 mol) of bisphenol A in Synthesis Example 1 was changed to 332 g (1.0 mol) of 1,1'-methylenebis-(2,7-naphthalenediol). The mass spectrum of this hydroxy compound B-7 was observed to have a peak of M+=979. From this, it was found to contain the hydroxy compound having the structure represented by the structural formula (b-10). The hydroxyl equivalent of this hydroxy compound B-7 calculated by GPC was 139 g/eq, and the average value of m in the structural formula (b-10) was 0.8.

Synthesis Example 8: Hydroxy Compound B-8 of C6 Type (BPA)

340 g of hydroxy compound B-8 was obtained by the same reaction as in Synthesis Example 1 except that 210 g (0.5 mol) of diglycidyl ether of 1,12-dodecanediol in Synthesis Example 1 was changed to 124 g (0.5 mol) of diglycidyl ether of 1,6-hexanediol (manufactured by DIC Corporation, trade name: EPICLON 726D, epoxy equivalent 124 g/eq). In the mass spectrum of this hydroxy compound B-8, a peak of M+=687 was found. The hydroxy equivalent of this hydroxy compound B-8 calculated by GPC was 262 g/eq.

Synthesis Example 9: Hydroxy Compound B-9 of C9 Type (BPA)

350 g of hydroxy compound B-9 was obtained by the same reaction as in Synthesis Example 1 except that 210 g (0.5 mol) of diglycidyl ether of 1,12-dodecanediol in Synthesis Example 1 was changed to 156 g (0.5 mol) of diglycidyl ether of 1,9-nonanediol (manufactured by Sakamoto Yakuhin Kogyo Co., Ltd., epoxy equivalent 156 g/eq). In the mass spectrum of this hydroxy compound B-9, a peak of M+=729 was found. The hydroxy equivalent of this hydroxy compound B-9 calculated by GPC was 328 g/eq.

Example 1: Epoxy Compound Ep-1 Using B-1

In a flask equipped with a thermometer, a dropping funnel, a cooling tube, and a stirrer, 330 g of hydroxy compound B-1 obtained in Synthesis Example 1, 1110 g (12.0 mol) of epichlorohydrin, and 280 g of n-butanol were charged and dissolved. After the temperature was raised to 65° C., the pressure was reduced to an azeotropic pressure, and 122 g (1.5 mol) of a 49% sodium hydroxide aqueous solution was added dropwise over 5 hours. Thereafter, stirring was continued for 0.5 hours under the same conditions. During this period, a fraction distilled by azeotropy was separated with a Dean-Stark trap, the aqueous layer was removed, and the reaction was carried out while returning the oil layer into the reaction system. Thereafter, unreacted epichlorohydrin was distilled off by distillation under reduced pressure. To the crude epoxy resin thus obtained, 1000 g of methyl isobutyl ketone and 100 g of n-butanol were added and dissolved. Further, 20 g of a 10% sodium hydroxide aqueous solution was added to this solution, and the mixture was reacted at 80° C. for 2 hours. After that, washing with 300 g of water was repeated three times until the pH of the washing solution became neutral. Then, the system was dehydrated by azeotropy, and after undergoing microfiltration, the solvent was distilled off under reduced pressure to obtain 350 g of epoxy compound Ep-1. The epoxy equivalent of the obtained epoxy compound Ep-1 was 425 g/eq. The epoxy resin (Ep-1) was found to contain the epoxy resin having the structure represented by the structural formula (A-1) by the NMR spectrum ($^{13}C$) and the obtaining of the peak at M+=883 corresponding to the theoretical structure of m=1, n=12, $p_1$=0, $p_2$=0, and q=1 in the structural formula (A-1) in the mass spectrum. The obtained epoxy resin (Ep-1) contained the compound of the structural formula (A-1) in which q=0, and as a result of confirmation by GPC, the compound of the structural formula (A-1) in which q=0 was contained at a ratio of 21% by mass in the mixture, and the average value of q in the structural formula (A-1) was 0.9.

Example 2: Epoxy Compound Ep-2 Using B-2

160 g of epoxy compound Ep-2 was obtained by the same reaction as in Example 1 except that 330 g of hydroxy compound B-1 obtained in Synthesis Example 1 was changed to 121 g of hydroxy compound B-2 obtained in Synthesis Example 2. The epoxy equivalent of the obtained epoxy compound Ep-2 was 195 g/eq. The epoxy resin (Ep-2) was found to contain the epoxy resin having the structure represented by the structural formula (A-8) by the NMR spectrum ($^{13}C$) and the obtaining of the peak at M+=791 corresponding to the theoretical structure of m=1, n=12, $p_1$=0, $p_2$=0, and q=1 in the structural formula (A-8) in the mass spectrum. The obtained epoxy resin (Ep-2) contained the compound of the structural formula (A-8) in which q=0, and as a result of confirmation by GPC, the compound of the structural formula (A-8) in which q=0 was contained at a ratio of 21% by mass in the mixture, and the average value of q in the structural formula (A-8) was 0.9.

Example 3: Epoxy Compound Ep-3 Using B-3

341 g of epoxy compound Ep-3 was obtained by the same reaction as in Example 1 except that 330 g of hydroxy compound B-1 obtained in Synthesis Example 1 was changed to 318 g of hydroxy compound B-3 obtained in Synthesis Example 3. The epoxy equivalent of the obtained epoxy compound Ep-3 was 413 g/eq. The epoxy resin (Ep-3) was found to contain the epoxy resin having the structure represented by the structural formula (A-3) by the NMR spectrum ($^{13}C$) and the obtaining of the peaks at M+=799, 856, and 912 corresponding to the theoretical structure of m=1, n=12, $p_1$=0, $p_2$=0, and q=1 in the structural formula (A-3) in the mass spectrum. The obtained epoxy resin (Ep-3) contained the compound of the structural formula (A-3) in which q=0, and as a result of confirmation by GPC, the compound of the structural formula (A-3) in which q=0 was contained at a ratio of 23% by mass in the mixture, and the average value of q in the structural formula (A-3) was 0.9.

Example 4: Epoxy Compound Ep-4 Using B-4

361 g of epoxy compound Ep-4 was obtained by the same reaction as in Example 1 except that 330 g of hydroxy compound B-1 obtained in Synthesis Example 1 was changed to 342 g of hydroxy compound B-4 obtained in Synthesis Example 4. The epoxy equivalent of the obtained epoxy compound Ep-4 was 432 g/eq. The epoxy resin (Ep-4) was found to contain the epoxy resin having the structure represented by the structural formula (A-3) by the NMR spectrum ($^{13}C$) and the obtaining of the peak at M+=912 corresponding to the theoretical structure of m=1, n=12, $p_1$=0, $p_2$=0, q=1, and the substituent R=$CH_3$ in the structural formula (A-3) in the mass spectrum. The obtained epoxy resin (Ep-4) contained the compound of the structural formula (A-3) in which q=0, and as a result of confirmation by GPC, the compound of the structural formula (A-3) in which q=0 was contained at a ratio of 28% by mass in the mixture, and the average value of q in the structural formula (A-3) was 0.9.

Example 5: Epoxy Compound Ep-5 Using B-5

310 g of epoxy compound Ep-5 was obtained by the same reaction as in Example 1 except that 330 g of hydroxy compound B-1 obtained in Synthesis Example 1 was changed to 271 g of hydroxy compound B-5 obtained in Synthesis Example 5. The epoxy equivalent of the obtained epoxy compound Ep-5 was 351 g/eq. The epoxy resin (Ep-5) was found to contain the epoxy resin having the structure represented by the structural formula (A-5) by the NMR spectrum ($^{13}C$) and the obtaining of the peak at M+=747 corresponding to the theoretical structure of m=1, n=12, $p_1$=0, $p_2$=0, and q=1 in the structural formula (A-5) in the mass spectrum. The obtained epoxy resin (Ep-5) contained the compound of the structural formula (A-5) in which q=0, and as a result of confirmation by GPC, the compound of the structural formula (A-5) in which q=0 was contained at a ratio of 20% by mass in the mixture, and the average value of q in the structural formula (A-5) was 0.9.

Example 6: Epoxy Compound Ep-6 Using B-6

221 g of epoxy compound Ep-6 was obtained by the same reaction as in Example 1 except that 330 g of hydroxy compound B-1 obtained in Synthesis Example 1 was changed to 192 g of hydroxy compound B-6 obtained in Synthesis Example 5. The epoxy equivalent of the obtained epoxy compound Ep-6 was 262 g/eq. The epoxy resin (Ep-6) was found to contain the epoxy resin having the structure represented by the structural formula (A-9) by the NMR spectrum ($^{13}C$) and the obtaining of the peak at M+=1124 corresponding to the theoretical structure of m=1, n=12, $p_1$=0, $p_2$=0, and q=1 in the structural formula (A-9) in the mass spectrum. The obtained epoxy resin (Ep-6) contained the compound of the structural formula (A-9) in which q=0, and as a result of confirmation by GPC, the compound of the structural formula (A-9) in which q=0 was contained at a ratio of 8% by mass in the mixture, and the average value of q in the structural formula (A-9) was 0.8.

Example 7: Epoxy Compound Ep-7 Using B-7

179 g of epoxy compound Ep-6 was obtained by the same reaction as in Example 1 except that 330 g of hydroxy compound B-1 obtained in Synthesis Example 1 was changed to 139 g of hydroxy compound B-7 obtained in Synthesis Example 5. The epoxy equivalent of the obtained epoxy compound Ep-7 was 194 g/eq. The epoxy resin (Ep-7) was found to contain the epoxy resin having the structure represented by the structural formula (A-10) by the NMR spectrum ($^{13}C$) and the obtaining of the peak at M+=1316 corresponding to the theoretical structure of m=1, n=12, $p_1$=0, $p_2$=0, and q=1 in the structural formula (A-10) in the mass spectrum. The obtained epoxy resin (Ep-7) contained the compound of the structural formula (A-10) in which q=0, and as a result of confirmation by GPC, the compound of the structural formula (A-10) in which q=0 was contained at a ratio of 21% by mass in the mixture, and the average value of q in the structural formula (A-10) was 0.7.

Comparative Example 1: Epoxy Compound Ep-8 Using B-8

380 g of epoxy compound Ep-8 was obtained by the same reaction as in Example 1 except that 330 g of hydroxy compound B-1 obtained in Synthesis Example 1 was changed to 262 g of hydroxy compound B-8 obtained in Synthesis Example 8. The epoxy equivalent of the obtained epoxy compound Ep-8 was 350 g/eq.

Comparative Example 2: Epoxy Compound Ep-9 Using B-9

350 g of epoxy compound Ep-9 was obtained by the same reaction as in Example 1 except that 330 g of hydroxy compound B-1 obtained in Synthesis Example 1 was changed to 262 g of hydroxy compound B-9 obtained in Synthesis Example 9. The epoxy equivalent of the obtained epoxy compound Ep-9 was 422 g/eq.

[Examples 8 to 14 and Comparative Examples 3 and 4] Preparation of Composition and Resin Cured Product The epoxy resin, the curing agent, and the curing accelerator were uniformly mixed in a mixer ("Awatori Rentaro ARV-200" manufactured by Thinky Corporation) according to the formulation shown in Table 1 to obtain a composition. This composition was sandwiched between aluminum mirror plates ("JIS H 4000 A1050P" manufactured by Engineering Test Service Co., Ltd.) using a silicon tube as a spacer, and heated and cured at 170° C. for 30 minutes to obtain a cured product having a thickness of 0.8 mm.
<Tensile Test>
The resin-cured product was punched into a dumbbell shape (JIS K 7161-2-1BA) with a punching blade, and this was used as a test piece. Using a tensile tester ("Autograph AG-IS" manufactured by Shimadzu Corporation), the test piece was evaluated for the tensile stress at break, the maximum strain rate, and the elastic modulus according to JIS K 7162-2 (test speed: 2 mm/min).
<Tensile Shear Test>
The resin composition was applied to one of two cold-rolled steel plates ("SPCC-SB" manufactured by TP Giken Co., Ltd., 1.0 mm×25 mm×100 mm), glass beads ("J-80" manufactured by Potters-Ballotini Co., Ltd.) were added as a spacer, and another one SPCC-SB plate was bonded (bonding area: 25 mm×12.5 mm). This was cured by heating at 170° C. for 30 minutes to obtain a test piece. Adhesiveness was evaluated by performing a tensile shear test using the test piece. The test was performed according to JIS K 6850, and the maximum point stress and the maximum point strain rate were compared.
<T-Type Peel Test>
The resin composition was applied to one of two cold-rolled steel plates ("SPCC-SB" manufactured by TP Giken Co., Ltd., 0.5 mm×25 mm×200 mm), glass beads ("J-80" manufactured by Potters-Ballotini Co., Ltd.) were added as a spacer, and another one SPCC-SB plate was bonded (bonding area: 25 mm×150 mm). This was cured by heating at 170° C. for 30 minutes to obtain a test piece. Adhesiveness was evaluated by performing a T-type peel test using the test piece. The test was performed according to JIS K 6854-3, and the average stress was compared.

TABLE 1

|  |  | Example | | | | | | | Comparative Example | |
|---|---|---|---|---|---|---|---|---|---|---|
|  |  | 8 | 9 | 10 | 11 | 12 | 13 | 14 | 3 | 4 |
| Epoxy resin | Ep-1 | 100 | | | | | | | | |
|  | Ep-2 | | 100 | | | | | | | |
|  | Ep-3 | | | 100 | | | | | | |
|  | Ep-4 | | | | 100 | | | | | |
|  | Ep-5 | | | | | 100 | | | | |
|  | Ep-6 | | | | | | 100 | | | |
|  | Ep-7 | | | | | | | 100 | | |
|  | Ep-8 | | | | | | | | 100 | |
|  | Ep-9 | | | | | | | | | 100 |
| Curing agent | DICY | 2.47 | 5.38 | 2.54 | 2.43 | 2.99 | 4.01 | 5.41 | 3 | 2.49 |
| Curing accelerator | DCMU | 0.85 | 0.85 | 0.85 | 0.85 | 0.85 | 0.85 | 0.85 | 0.85 | 0.85 |
| Tensile test | Tensile stress at break (MPa) | 22 | 26 | 42 | 28 | 31 | 26 | 53 | 25 | 23 |
|  | Maximum strain rate (%) | 163 | 132 | 35 | 52 | 56 | 98 | 42 | 4 | 7 |
|  | Elastic modulus (MPa) | 40 | 70 | 1400 | 850 | 840 | 90 | 1750 | 1760 | 1400 |
| Tensile shear test | Maximum point stress (MPa) | 21 | 20 | 17 | 19 | 17 | 20 | 16 | 9 | 7 |
|  | Maximum point strain rate (%) | 2.8 | 1.9 | 1.2 | 1.5 | 1.2 | 1.8 | 1.2 | 0.9 | 0.6 |
| T-type peel test | Average stress (N/mm) | 5.9 | 3.5 | 1.1 | 1.8 | 2.6 | 3.1 | 1.3 | 0.6 | 0.4 |

The materials used in the table are as follows.

DICY: Dicyandiamide ("DICY7" manufactured by Mitsubishi Chemical Corporation)

DCMU: 3-(3,4-dichlorophenyl)-1,1-dimethylurea ("B-605-IM" manufactured by DIC Corporation)

As shown in Examples 8 to 14, the present invention has a high strain rate in a tensile test and a high adhesive force in a tensile shear test and a T-type peel test.

Since Examples 8, 9, and 13 have a low elastic modulus, these examples can be suitably used particularly for applications requiring cushioning properties. In addition, since Examples 10, 11, 12, and 14 have a high elastic modulus, these examples can be suitably used particularly for applications requiring rigidity imparting.

<Measurement of Amount of Warpage when Bonding Different Materials>

The epoxy resin, the curing agent, and the curing accelerator were uniformly mixed in a mixer ("Awatori Rentaro ARV-200" manufactured by Thinky Corporation) according to the formulation shown in Table 2 to obtain a composition. The resin composition was applied to an aluminum plate ("A6061P-T6" manufactured by Engineering Test Service Co., Ltd., 2 mm×25 mm×100 mm), glass beads ("J-80" manufactured by Potters-Ballotini Co., Ltd.) were added as a spacer, and CFRP ("CFRP (epoxy)" manufactured by Engineering Test Service Co., Ltd., 1 mm×25 mm×100 mm) was bonded (bonding area: 25 mm×100 mm). This was cured by heating at 170° C. for 30 minutes, and the amount of warpage of the bonded test piece was measured. The amount of warpage was measured by stretching a water thread from the center in the lateral direction of the test piece to the entire length in the longitudinal direction, and measuring the distance between the valley bottom at the center in the longitudinal direction and the water thread as the amount of warpage.

TABLE 2

|  |  | Example 15 | Comparative Example 5 |
|---|---|---|---|
| Epoxy resin | Ep-1 | 100 |  |
|  | E-850S |  | 100 |
| Curing agent | DICY | 2.47 | 5.59 |
| Curing accelerator | DCMU | 0.85 | 0.85 |
| Amount of warpage | mm | 0.2 | 1.5 |

The materials used in the table are as follows.

E-8505: Bisphenol A type epoxy resin (manufactured by DIC Corporation, epoxy equivalent 188 g/eq)

DICY: Dicyandiamide ("DICY7" manufactured by Mitsubishi Chemical Corporation)

DCMU: 3-(3,4-dichlorophenyl)-1,1-dimethylurea ("B-605-IM" manufactured by DIC Corporation)

As shown in Example 15, it was shown that the present invention can reduce the warpage that occurs when different kinds of materials are bonded.

INDUSTRIAL APPLICABILITY

The epoxy compound A of the present invention can provide a flexible cured product having both a high elongation based on elastic deformation and a high adhesiveness capable of withstanding a difference in thermal expansion from the substrate. In particular, it can be suitably used for adhesives for structural materials, and advanced electronic materials such as semiconductor encapsulating materials and insulating layers for multilayer printed circuit boards.

The invention claimed is:

1. An epoxy compound A prepared by:
   reacting a hydroxy compound B with an epihalohydrin (a3);
   wherein the hydroxy compound B is formed by reacting a diglycidyl ether (a1) of an aliphatic dihydroxy compound and an aromatic hydroxy compound (a2) at a molar ratio (a1)/(a2) in the range of 1/1.01 to 1/5.0;
   wherein the aliphatic dihydroxy compound is represented by the following structure:

$$HO-\left(\underset{R_2}{\overset{R_1}{\underset{|}{\overset{|}{C}}}}\right)_n-OH$$

where $R_1$ and $R_2$ each independently represent a hydrogen atom or an alkyl group having 1 or 2 carbon atoms, and n is an integer of 11 to 16;
   wherein the aromatic hydroxy compound (a2) is represented by the following structure:

HO—Ar—OH where Ar is an unsubstituted or substituted aromatic structure; and
   wherein the hydroxy compound B is represented by the following structure:

$$HO-Ar-\left[O\underset{R_{10}}{\overset{R_6}{\vee}}O-\left(\underset{R_2}{\overset{R_1}{\underset{|}{\overset{|}{C}}}}\right)_n-O\underset{R_{11}}{\overset{R_7}{\vee}}O-Ar\right]_m-OH$$

where $R_6$ and $R_7$ each represent a hydroxyl group, $R_{10}$ and $R_{11}$ each independently represent a hydrogen atom or a methyl group, and m is an average value of repetition and is 0.5 to 10.

2. The epoxy compound A according to claim 1, wherein both terminal OH groups of the hydroxy compound B have been reacted to form terminal glycidyl ether groups.

3. The epoxy compound A according to claim 2, wherein Ar is any aromatic structure represented by the following formula (2):

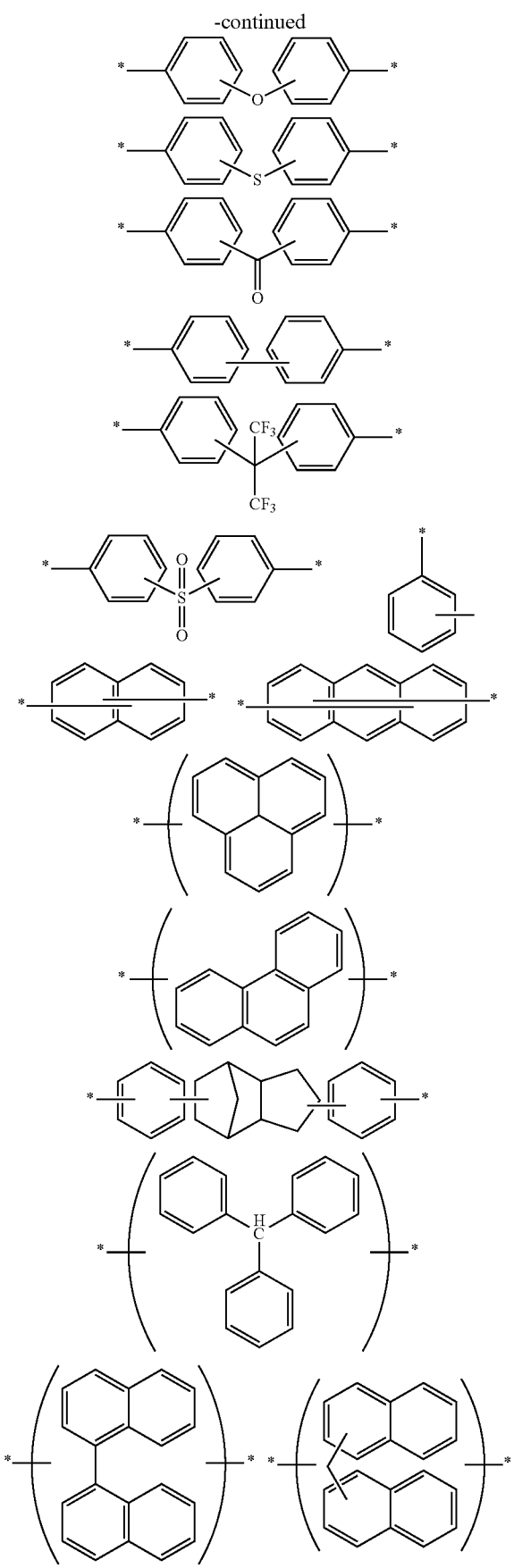

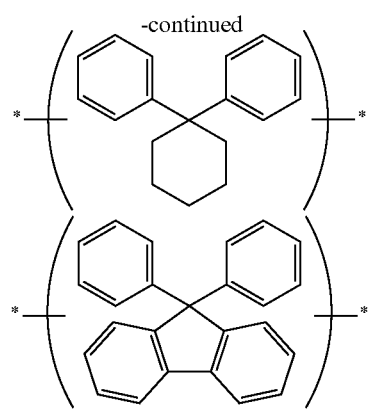

in the formula (2), the aromatic structure may be substituted or unsubstituted, and * represents a bonding point.

4. The epoxy compound A according to claim 2, wherein Ar is an aromatic structure substituted by a hydroxyl group.

5. A composition comprising the epoxy compound A according to claim 2.

6. The epoxy compound A according to claim 1, wherein Ar is any aromatic structure represented by the following formula (2):

(2)

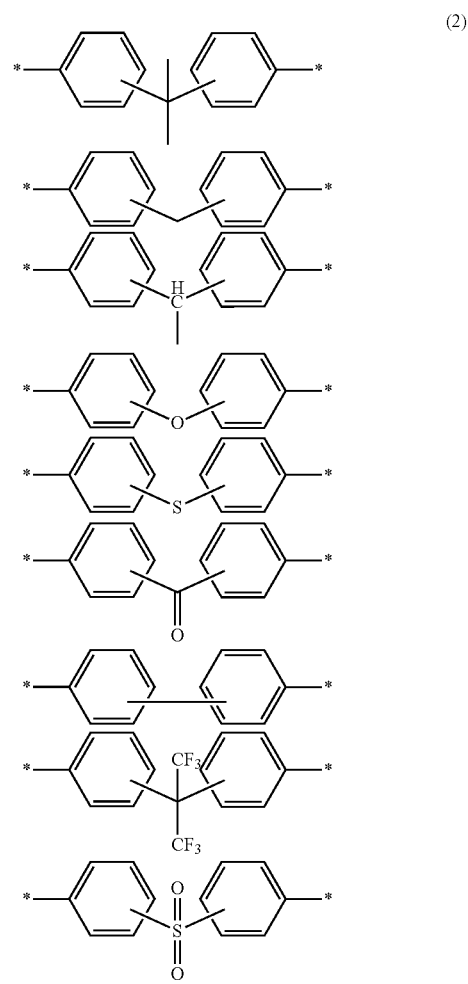

-continued

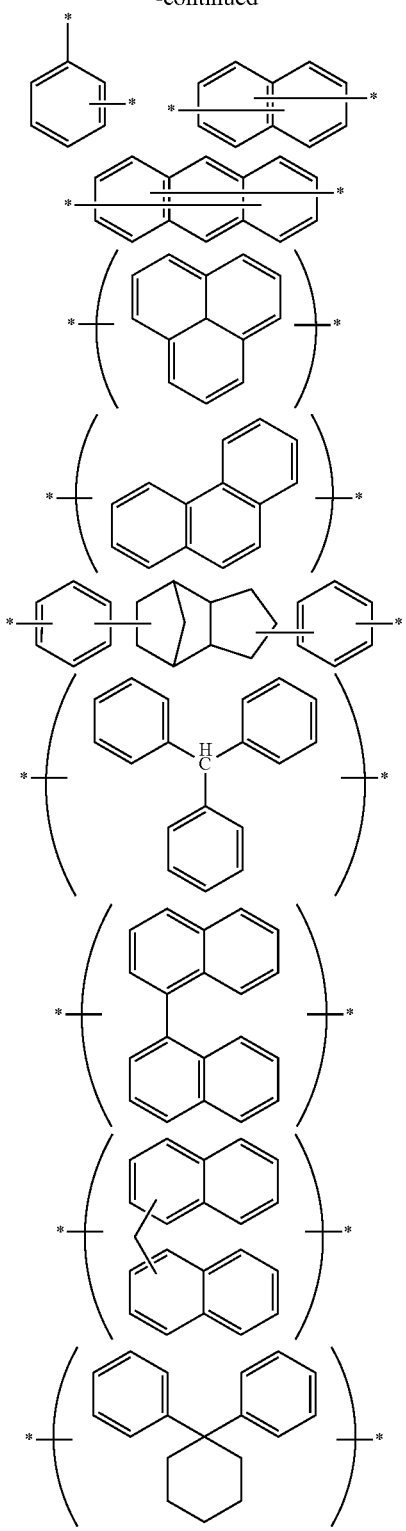

-continued

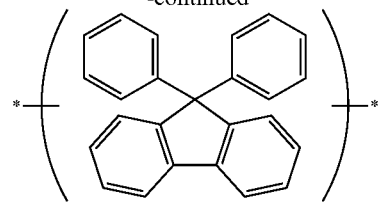

in the formula (2), the aromatic structure may be substituted or unsubstituted, and * represents a bonding point.

7. The epoxy compound A according to claim 6, wherein Ar is an aromatic structure substituted by a hydroxyl group.

8. A composition comprising the epoxy compound A according to claim 6.

9. The epoxy compound A according to claim 1, wherein Ar is an aromatic structure substituted by a hydroxyl group.

10. A composition comprising the epoxy compound A according to claim 9.

11. A composition comprising the epoxy compound A according to claim 1.

12. A composition comprising the epoxy compound A according to claim 1 and a curing agent.

13. The composition according to claim 12, wherein the curing agent is at least one selected from an amine compound, a phenol compound, a carboxylic acid compound, and an acid anhydride compound.

14. The composition according to claim 12, further comprising a filler.

15. A cured product obtained by curing the composition according to claim 12.

16. A laminate comprising a substrate and a layer of the cured product according to claim 15.

17. The laminate according to claim 16, wherein the substrate is a metal or a metal oxide.

18. An electronic member comprising the laminate according to claim 16.

19. A laminate comprising a substrate, a second substrate, and a layer of the cured product according to claim 15, wherein the laminate is formed by laminating the substrate, the layer of the cured product, and the second substrate in this order, wherein the substrate is a metal or a metal oxide, and the second substrate is a plastic layer.

20. An adhesive for a metal or a metal oxide, comprising the epoxy compound A according to claim 1 and at least one of a curing agent and a curing accelerator.

21. A composition comprising the epoxy compound A according to claim 1 and a curing accelerator.

22. A cured product obtained by curing the composition according to claim 21.

23. A composition comprising the epoxy compound A according to claim 1, a curing agent, and a curing accelerator.

24. A cured product obtained by curing the composition according to claim 23.

* * * * *